US012658290B2

(12) United States Patent
Shah

(10) Patent No.: US 12,658,290 B2
(45) Date of Patent: *Jun. 16, 2026

(54) TEAM-BASED TELE-DIAGNOSTICS BLOCKCHAIN-ENABLED SYSTEM

(71) Applicant: Netspective Communications LLC, Silver Spring, MD (US)

(72) Inventor: Shahid N. Shah, Silver Spring, MD (US)

(73) Assignee: Intellectual Frontiers LLC, Silver Spring, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/232,314

(22) Filed: Aug. 9, 2023

(65) Prior Publication Data

US 2024/0006038 A1 Jan. 4, 2024

Related U.S. Application Data

(63) Continuation of application No. 16/161,846, filed on Oct. 16, 2018, now Pat. No. 11,769,573.

(51) Int. Cl.
*G16H 10/60* (2018.01)
*G06F 16/182* (2019.01)
(Continued)

(52) U.S. Cl.
CPC ......... *G16H 10/60* (2018.01); *G06F 16/1824* (2019.01); *G06F 16/27* (2019.01);
(Continued)

(58) Field of Classification Search
CPC ........ G16H 10/60; G16H 40/67; G16H 50/20; G06F 16/1824; G06F 16/27;
(Continued)

(56) References Cited

U.S. PATENT DOCUMENTS 6,006,191 A 12/1999 DiRienzo
6,454,709 B1 9/2002 Kleinschmidt et al.
(Continued)

FOREIGN PATENT DOCUMENTS

JP 2007241589 A 9/2007
WO 2018039312 A1 3/2018

OTHER PUBLICATIONS

Meyer, A., et al., "Crowdsourcing Diagnosis for Patients With Undiagnosed Illnesses: An Evaluation of CrowdMed," Journal of Medical Internet Research, 18.1, Jan. 14, 2016, e12, 12 pages.

*Primary Examiner* — Rachelle L Reichert
*Assistant Examiner* — Amanda R. Covington
(74) *Attorney, Agent, or Firm* — Rahman LLC

(57) ABSTRACT

A computer-controlled diagnostic network system. The system includes diagnostic devices and diagnostician devices located at different locations in a distributed secured network. The system includes a computer-controlled central blockchain server for storing and processing details obtained from the diagnostic devices and the diagnostician devices. The computer-controlled central blockchain server is communicatively coupled to a data extraction device for retrieving a plurality of computer-executable files stored at discrete distributed locations associated with one or more users of the distributed secured network. The computer-controlled central blockchain server is communicatively coupled to a blockchain device to process blockchain tasks through blockchain-enabled and computer-controlled software and hardware tools. The computer-controlled central blockchain server is located at a location remote from the locations of the diagnostic devices and the diagnostician devices.

20 Claims, 11 Drawing Sheets

(51) Int. Cl.

| | |
|---|---|
| *G06F 16/27* | (2019.01) |
| *G16H 40/67* | (2018.01) |
| *G16H 50/20* | (2018.01) |
| *H04L 9/00* | (2022.01) |
| *H04L 9/06* | (2006.01) |
| *H04L 9/32* | (2006.01) |

(52) U.S. Cl.

CPC ............. *G16H 40/67* (2018.01); *G16H 50/20* (2018.01); *H04L 9/0643* (2013.01); *H04L 9/3236* (2013.01); *H04L 9/3297* (2013.01); *H04L 9/50* (2022.05); *H04L 2209/00* (2013.01)

(58) Field of Classification Search

CPC ... H04L 9/0643; H04L 9/3236; H04L 9/3297; H04L 9/50; H04L 2209/00

See application file for complete search history.

(56) References Cited

U.S. PATENT DOCUMENTS

| | | | | |
|---|---|---|---|---|
| 8,407,254 | B2 | 3/2013 | DiRienzo | |
| 8,949,136 | B2 | 2/2015 | Heyman | |
| 2009/0204470 | A1* | 8/2009 | Weyl | G06Q 10/06 |
| | | | | 705/7.13 |
| 2012/0245952 | A1 | 9/2012 | Halterman et al. | |
| 2013/0326639 | A1 | 12/2013 | Droste et al. | |
| 2014/0073880 | A1 | 3/2014 | Boucher et al. | |
| 2015/0332196 | A1* | 11/2015 | Stiller | G16H 20/40 |
| | | | | 705/2 |
| 2015/0370985 | A1 | 12/2015 | Carvalko et al. | |
| 2016/0125152 | A1 | 5/2016 | Higgs | |
| 2017/0103472 | A1 | 4/2017 | Shah | |
| 2017/0330180 | A1* | 11/2017 | Song | G06Q 20/401 |
| 2018/0060496 | A1* | 3/2018 | Bulleit | H04L 9/0643 |
| 2018/0137244 | A1* | 5/2018 | Sorenson | A61B 8/565 |

* cited by examiner

TASK SEGMENTATION ENGINE 502

TASK SCHEDULING ENGINE 504

CONDITION DESIGNER 506

WORKFLOW ANALYZER 508

RULES-BASED ENGINE 510

STATISTICAL ANALYZER 512

WORKFLOW SYSTEM 310

FIG. 6

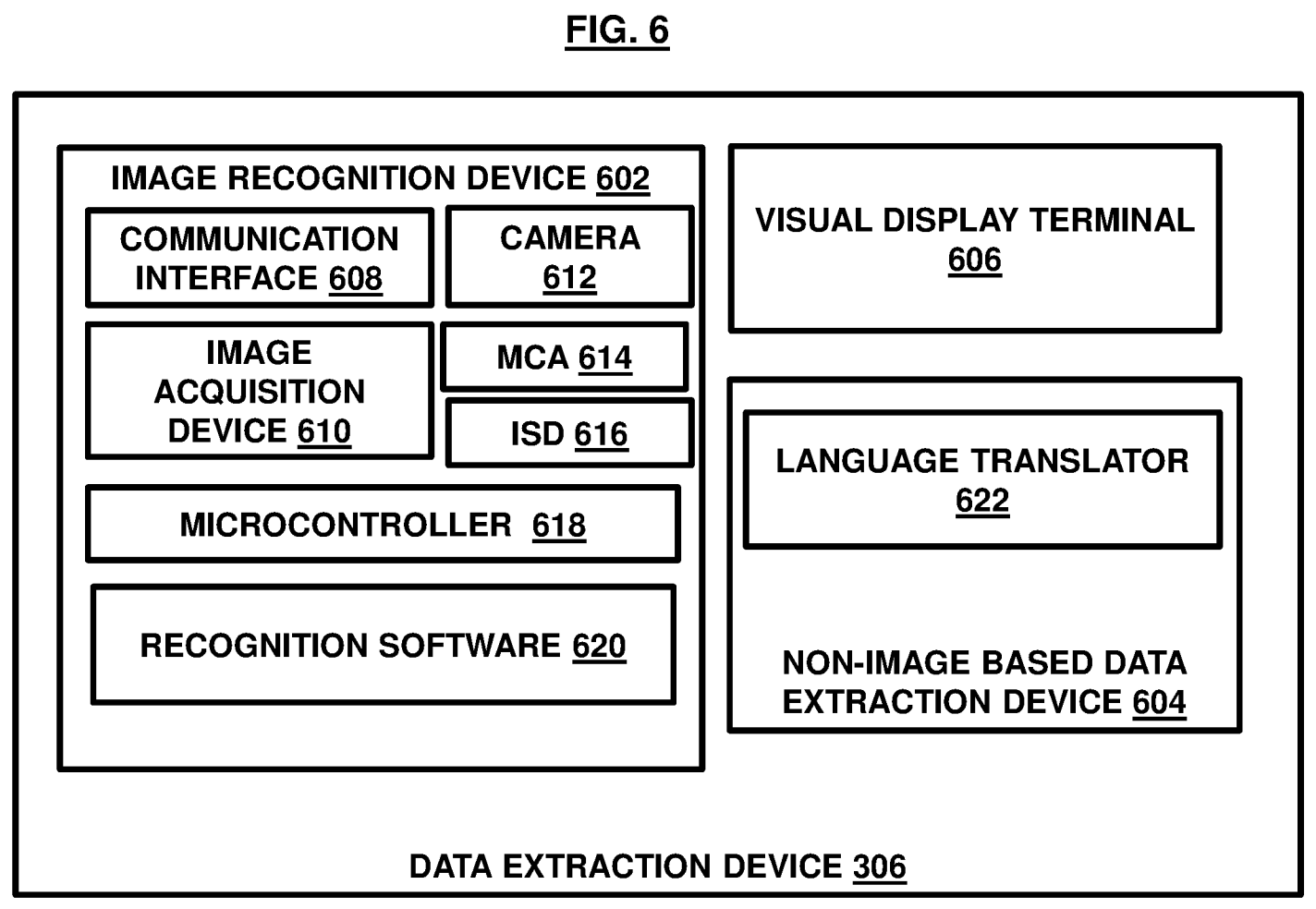

DATA EXTRACTION DEVICE 306

IMAGE RECOGNITION DEVICE 602

COMMUNICATION INTERFACE 608

CAMERA 612

IMAGE ACQUISITION DEVICE 610

MCA 614

ISD 616

MICROCONTROLLER 618

RECOGNITION SOFTWARE 620

VISUAL DISPLAY TERMINAL 606

NON-IMAGE BASED DATA EXTRACTION DEVICE 604

LANGUAGE TRANSLATOR 622

FIG. 7

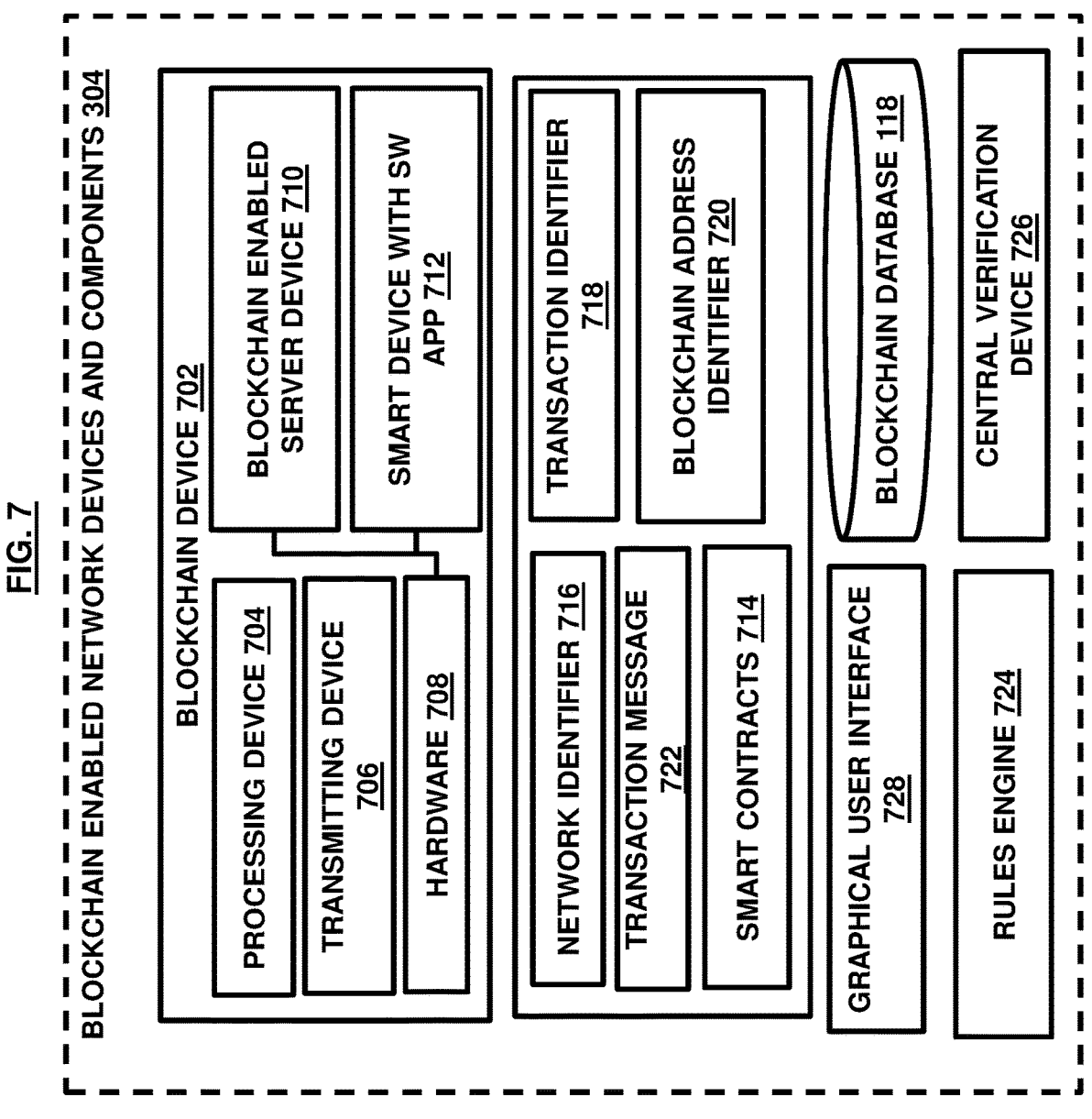

BLOCKCHAIN ENABLED NETWORK DEVICES AND COMPONENTS 304

BLOCKCHAIN DEVICE 702

BLOCKCHAIN ENABLED SERVER DEVICE 710

SMART DEVICE WITH SW APP 712

PROCESSING DEVICE 704

TRANSMITTING DEVICE 706

HARDWARE 708

TRANSACTION IDENTIFIER 718

BLOCKCHAIN ADDRESS IDENTIFIER 720

NETWORK IDENTIFIER 716

TRANSACTION MESSAGE 722

SMART CONTRACTS 714

BLOCKCHAIN DATABASE 118

GRAPHICAL USER INTERFACE 728

CENTRAL VERIFICATION DEVICE 726

RULES ENGINE 724

Figure 11:
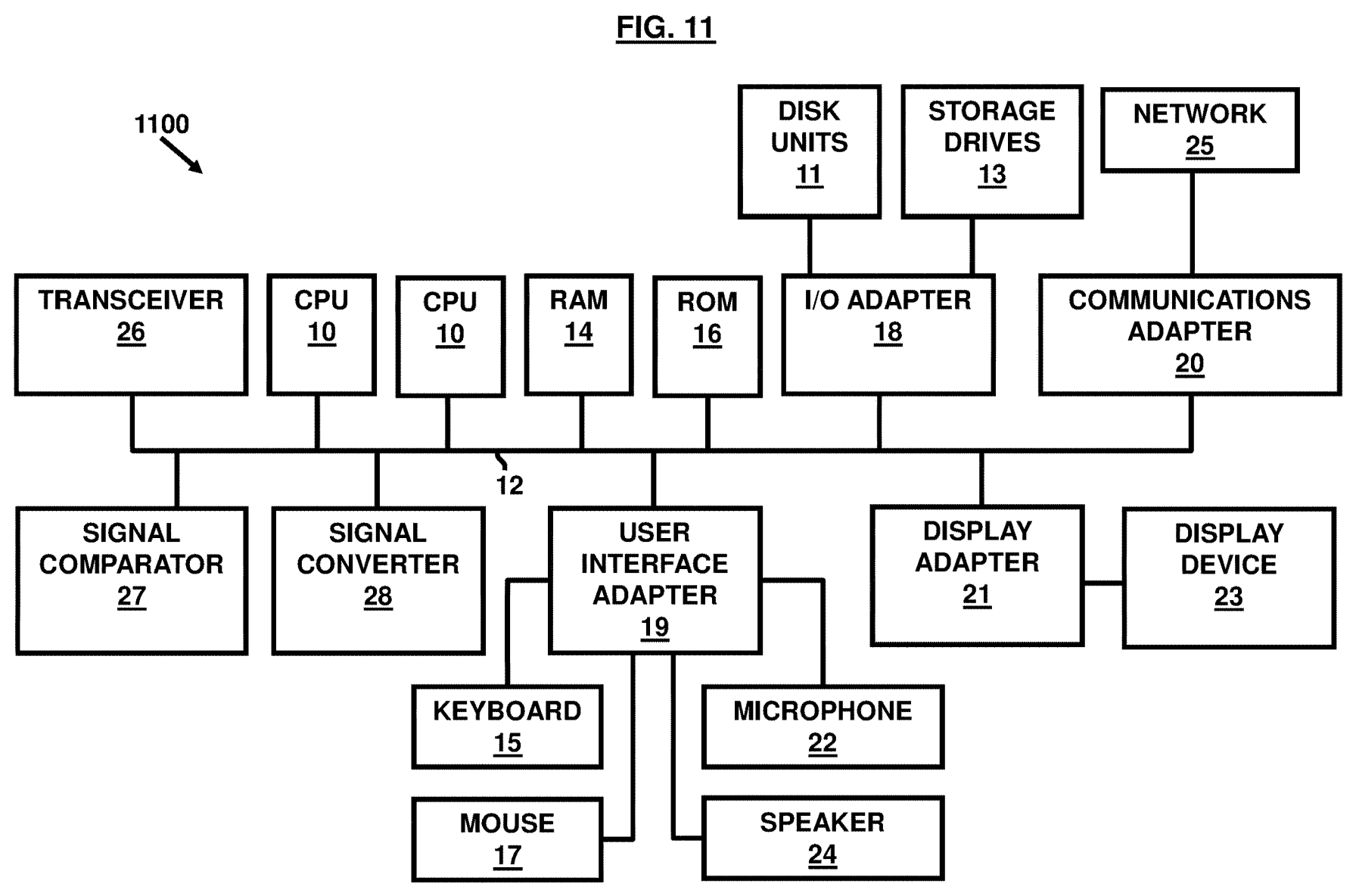

NETWORK
25

COMMUNICATIONS
ADAPTER
20

DISPLAY
DEVICE
23

STORAGE
DRIVES
13

DISK
UNITS
11

I/O ADAPTER
18

DISPLAY
ADAPTER
21

MICROPHONE
22

SPEAKER
24

ROM
16

RAM
14

CPU
10

CPU
10

USER
INTERFACE
ADAPTER
19

KEYBOARD
15

MOUSE
17

12

TRANSCEIVER
26

SIGNAL
CONVERTER
28

SIGNAL
COMPARATOR
27

TEAM-BASED TELE-DIAGNOSTICS BLOCKCHAIN-ENABLED SYSTEM

CROSS-REFERENCE TO RELATED APPLICATIONS

This application is a continuation of U.S. patent application Ser. No. 16/161,846 filed on Oct. 16, 2018, the complete disclosure of which, in its entirety, is hereby incorporated by reference.

BACKGROUND

Technical Field

The embodiments herein generally relate to secured computer-controlled networks, and more particularly to a blockchain-enabled computer-controlled diagnostic network for executing team-based tele-diagnostic tasks.

Description of the Related Art

In diagnostic networks, various entities typically manage their networked devices manually in a combined setup. For example, the devices, device operators, device managers, respondents, and gathered data are all located at a single location. This does not allow enough flexibility to operate with distributed networked users who can otherwise access and execute a set of workflow tasks on the data gathered from the devices. Generally, there is adequate conventional system to provide enhanced distributed diagnostic network of users to perform various diagnostic operations in a distributed setup such that the users are not combined at one location.

Therefore, in light of the above, there is a need of a system and a method for providing a distributed mechanism to allow the users within the distributed diagnostic network system and associated devices to operate from remote locations over a secured network that allows independence and security of data that may not be tampered and can be relied upon by the distributed users of the diagnostic network.

SUMMARY

In view of the foregoing, an embodiment herein provides a computer-controlled diagnostic network system to facilitate integrated remote-based diagnostics. The system includes a first diagnostic device located at a first location in a distributed secured network, a second diagnostic device located at a second location in the distributed secured network and remotely located from the first diagnostic device, a first diagnostician device associated with a first diagnostician located at a third location in the distributed secured network and remotely located from the first diagnostic device and the second diagnostic device, a second diagnostician device associated with a second diagnostician located at a fourth location in the distributed secured network and remotely located from the first diagnostic device, the second diagnostic device, and the third diagnostician device, and a computer-controlled central blockchain server for storing and processing details obtained from the first diagnostic device, the second diagnostic device, the first diagnostician device, and the second diagnostician device. The computer-controlled central blockchain server is communicatively coupled to a data extraction device for retrieving a plurality of computer-executable files stored at discrete distributed locations associated with one or more users of the distributed secured network. At least one of the one or more users is associated with a computer system operatively coupled to an installable extraction agent. The computer-controlled central blockchain server is communicatively coupled to a blockchain device to process blockchain tasks through blockchain-enabled and computer-controlled software and hardware tools. The computer-controlled central blockchain server is located at a location remote from the locations of the first diagnostic device, the second diagnostic device, the first diagnostician device, and the second diagnostician device. The system includes a secured cloud server to allow the one or more users to access one or more of the computer-executable files through a secured access from a remote location without being able to create a local copy of the one or more of the computer-executable files stored within the computer-controlled central blockchain server.

The plurality of computer-executable files may contain digitally stored data generated and retrieved from the first diagnostic device and the second diagnostic device.

The system may further include a standardizing device to perform computer-executable digital instructions for standardizing the digitally stored data retrieved from the first diagnostic device and the second diagnostic device in accordance with a predefined format, wherein the digitally stored data before standardizing may reside in a plurality of formats within the first diagnostic device and the second diagnostic device.

The system may include a blockchain database communicatively coupled to the computer-controlled central blockchain server and located at a location remotely from the locations of the first diagnostic device, the second diagnostic device, the first diagnostician device and the second diagnostician device.

The data extraction device may be communicatively coupled to a workflow system. The workflow system may be configured to perform a set of special purpose-based computer-executable operations for performing a plurality of computer-controlled tasks within the distributed secured network.

The plurality of computer-executable tasks within the distributed network may include creating one or more work flow steps for a set of workflow tasks, defining a set of routing rules for one or more of the users associated with the first diagnostician device and the second diagnostician device that trigger or accept to execute a certain workflow task, retrieving the work flow tasks for allocation from the blockchain database where the data extracted from the first diagnostic device and the second diagnostic device is stored, and presenting digitally one or more of the workflow tasks to the users based on their credentials and their preferences as indicative in their registered profiles.

The workflow system may further include a task segmentation engine to create the one or more work flow steps for the set of workflow tasks defining a set of routing rules for the one or more of the users that trigger or accept to execute the workflow task digitally. The workflow system may further include a task scheduling engine to allocate and present the one or more workflow tasks to the users based on their credentials and their preferences as indicative in their registered profiles. The distributed secured network may be a blockchain configured diagnostic network.

The data extraction device may further include an image recognition device and a non-image-based data extraction device. The image recognition device may be configured to read, recognize and extract image-based data from the data extraction device, and the non-image-based data extraction device may be configured to read, recognize, and extract the non-image-based data from the first diagnostic device and the second diagnostic device. The image recognition device may further include a communication interface for establishing communication with a plurality of components of the computer-controlled central blockchain server; an image acquisition device to receive digital signals containing image patterns and expressions and to read image-based data obtained from one or more of the first diagnostic device, second diagnostic device, first diagnostician device, and the second diagnostician device; a camera for taking still or streaming images of the data being extracted by the data extraction device; and a plurality of multichannel amplifiers (MCA) such that each amplifier of the multichannel amplifiers may be defined to receive a specific type of sensed information from the camera allowing sourcing of signals for the image recognition device.

The blockchain device may further include a processing device to process blockchain tasks through computer-controlled software and hardware tools.

The blockchain device may further include a transmitting device to allow transmission of the computer-executable files from the computer-controlled central blockchain server to the secured cloud server and to one or more of the users and associated one or more of the first diagnostician device and the second diagnostician device as allowed within the diagnostic network based on permissions and access rights.

The blockchain device may further include a central verification device configured to verify identity information of one or more of the first diagnostician device and the second diagnostician device in the secured network through which a user requests to access a workflow task for execution. The system may further include a credentialing system to compute credentialing of a registered profile associated with the user such that the access is granted based on credentialing of the registered profile.

The system may further include an artificial intelligence (AI) system integrated within the computer-controlled central blockchain server, wherein the AI system enables an artificially intelligent diagnostic network within the distributed secured network. The AI system may further include an interface layer to receive inputs form a computing system that serves as an initial input to the AI system. The AI system may further include an AI application processing layer to collect the initial inputs and related information from the blockchain database and external Internet sources, and process the initial inputs, make automated analysis and judgment for automated reading of the data extracted from the first diagnostic device and the second diagnostic devices using computational intelligent tools. The AI system may allow to process execution of a workflow task automatically using inputs generated based on the initial inputs at a second state when the initial inputs are evolved using a set of computational intelligence tools.

An embodiment herein provides a system for managing a diagnostic network including a plurality of digitally configured users to facilitate integrated remote-based diagnostics. The system includes a data extraction device retrieving computer-executable files from one or more of the plurality of users, wherein the plurality of users include one or more of a first networked system associated with a first diagnostician device, a second networked system associated with a second diagnostic device, a third networked system associated with a first diagnostician device, a fourth networked system associated with a second diagnostician device. Each of the first diagnostic device, the second diagnostic device, the first diagnostician device, and the second diagnostician device are located remote from one another at physically distributed locations. The system includes a workflow system for generating a computer-executable workflow file indicative of tasks allocation among the one or more of the plurality of users connected through the diagnostic network, wherein the computer-executable workflow file identify nature of tasks for execution digitally by the one or more of the plurality of users, automated access rights depending on credentialing of digital profiles of the one or more of the plurality of users, and monetary benefits after the execution of the workflow tasks allocated to the one or more of the plurality of users. The workflow tasks allocation is updated dynamically in the computer-executable workflow file when a user of the plurality of users accepts an allocation out of the workflow tasks presented to the user.

The system further includes a computer-controlled central blockchain server for storing and processing details obtained from the first diagnostic device, the second diagnostic device, the first diagnostician device, and the second diagnostician device. The computer-controlled central blockchain server is communicatively coupled to the data extraction device for retrieving the computer-executable files stored at discrete distributed locations associated with the one or more users of the distributed secured network. The computer-controlled central blockchain server is further communicatively coupled to a blockchain device. The system further includes a secured cloud server to allow the one or more users to access one or more of the computer-executable files through a secured access from a remote location without being able to create a local copy of the one or more of the computer-executable files.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 6 illustrates various components of a data extraction device in accordance with an embodiment herein;

FIG. 7 illustrates various blockchain-enabled network devices and components in accordance with an embodiment herein;

FIG. 11 is a block diagram illustrating a computer system according to an embodiment herein.

DETAILED DESCRIPTION

Figure 1:
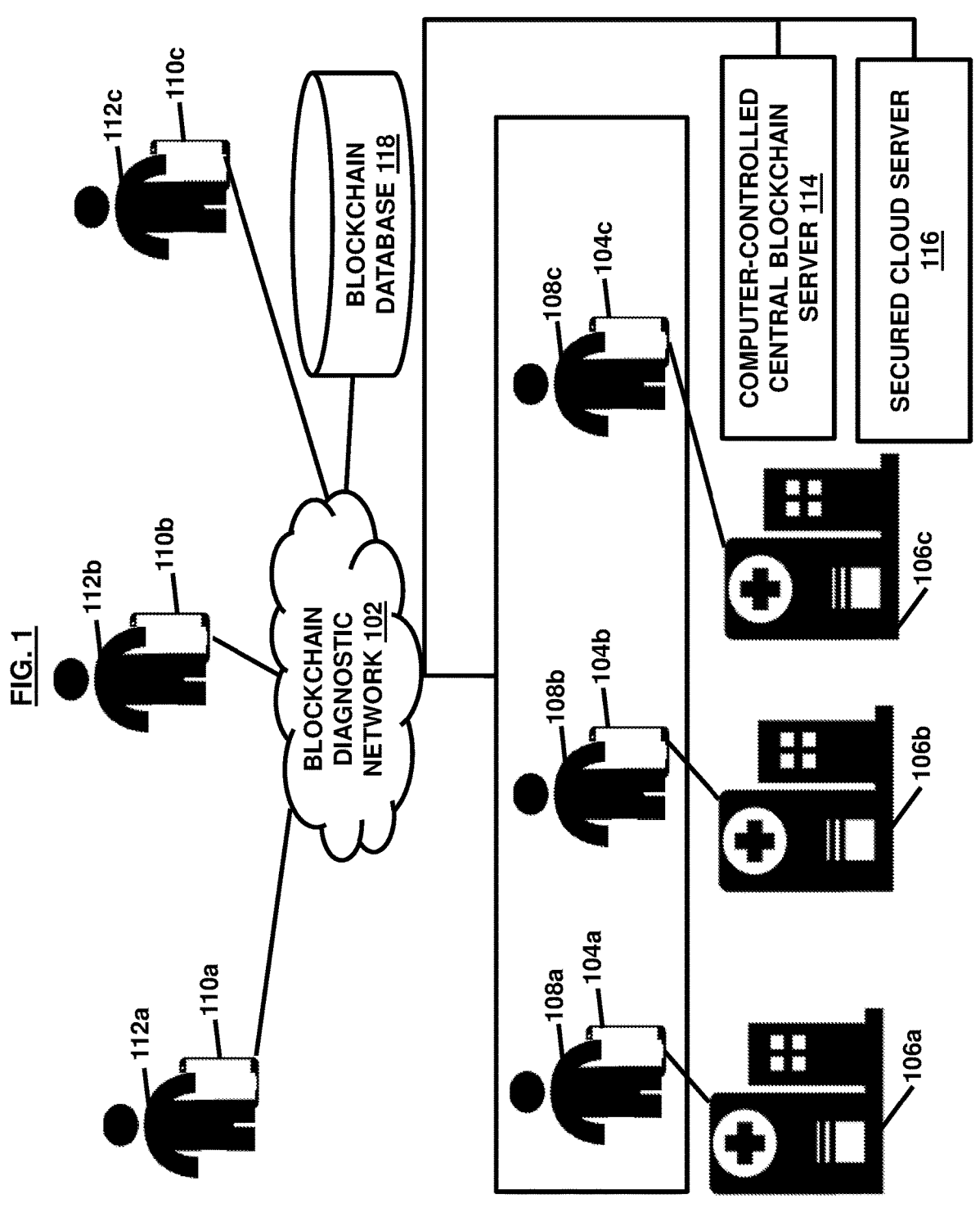
FIG. 1 illustrates, among other things, an example of an environment or architecture in which various embodiments herein may operate.

The embodiments herein and the various features and advantageous details thereof are explained more fully with reference to the non-limiting embodiments that are illustrated in the accompanying drawings and detailed in the following description. Descriptions of well-known components are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein provide a system and method for managing a diagnosis network 102 (shown in FIG. 1) containing a plurality of users. The users are associated with the diagnostic network 102 through computer-controlled systems such as digital devices including computer systems, laptops, smart phones, mobile devices, internet-of-things (IoT)-enabled smart devices for performing intelligent or computerized operations, smart utility devices, and other forms of computing machines and the like. Referring now to the drawings, and more particularly to FIGS. 1 through 11, where similar reference characters denote corresponding features consistently throughout the figures, there are shown preferred embodiments.

FIG. 1 illustrates generally, but not by way of limitation, among other things, an example of an environment or architecture 100 in which various embodiments herein may operate. As illustrated in FIG. 1, the environment 100 comprises a blockchain-configured diagnostic network 102 also referred to as blockchain network or diagnostic network 102 for the purpose of simplicity without limitations, a first user (such as a first diagnostic device 104a associated with a first diagnostic center 106a and a first data source 108a), a second user (such as a second diagnostic device 104b associated with a second diagnostic center 106b and a second data source 108b), a third user (such as a third diagnostic device 104c associated with a third diagnostic center 106c and a third data source 108c), a fourth user (a first diagnostician device 110a associated with a first diagnostician 112a), a fifth user (a second diagnostician device 110b associated with a second diagnostician 112b), a sixth user (a third diagnostician device 110c associated with a third diagnostician 112c). Similarly, more diagnostician devices and diagnostic devices may be connected within the blockchain network 102. The blockchain network 102 as shown in FIG. 1 may be termed as diagnostic network 102 alternatively throughout the disclosure that follows.

The diagnostic network 102 may also include a plurality of data sources such as the first data source 108a, the second data source 108b, and the third data source 108c. The diagnostic network 102 may also include a plurality of diagnostic centers (including the first diagnostic center

106a, the second diagnostic center 106b, and the third diagnostic center 106c) such as including without limitations hospitals, medical clinics, etc. that are configured and equipped to digitally process a variety of diagnostic operations digitally.

The diagnostic network 102 may also include a computer controlled central blockchain server 114 and a secured cloud server 116. The computer controlled central blockchain server 114 also referred to as blockchain server 114 alternatively for the purpose of simplicity of description is configured to perform a set of operations within the blockchain network 102. For example, the blockchain server 114 may store and process details obtained from the various diagnostic devices together referred to as 104 and the diagnostician devices together referred to as 110. The blockchain server 114, along with other connected or included devices, may be configured to retrieve a plurality of computer-executable files stored at discrete distributed locations associated with one or more users of the blockchain network 102. The blockchain server 114 may be communicatively coupled to the secured cloud server 116 in some embodiments.

The secured cloud server 116 allows the users to access one or more of the computer-executable files through a secured access from a remote location without being able to create a local copy of the one or more of the computer-executable files.

Figure 2:
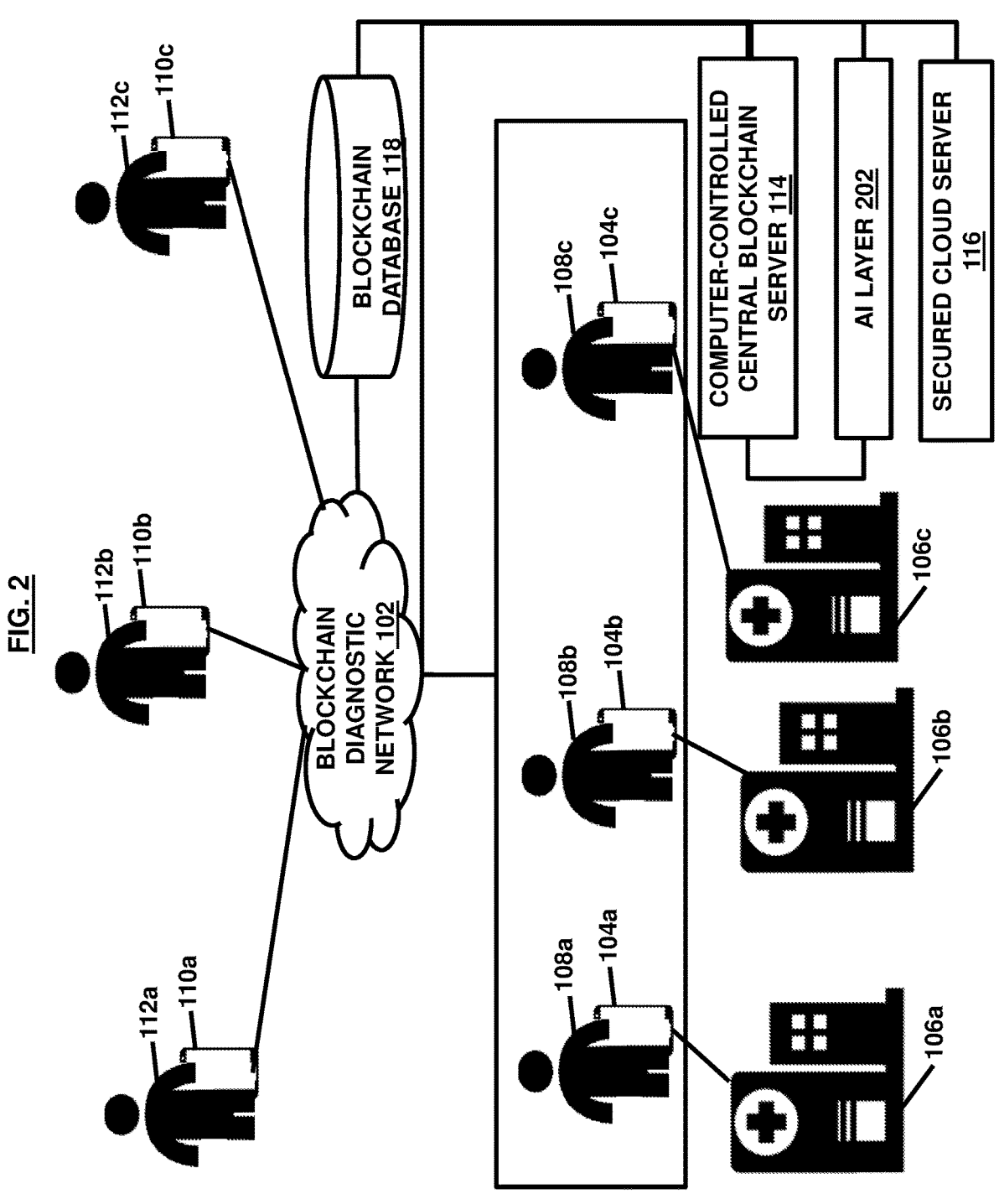
FIG. 2 illustrates, among other things, another example of an environment or architecture in which various embodiments herein may operate.

FIG. 2, with reference to FIG. 1, illustrates generally, but not by way of limitation, among other things, an example of an environment or architecture 200 in which at least some embodiments herein may operate. The architecture 200 may additionally include an AI layer 202 along with other components and devices as discussed in conjunction with FIG. 1. The AI layer 202 is described later in conjunction with FIG. 8.

Various devices and associated methods of FIGS. 1 and 2 are now discussed hereafter in conjunction with FIGS. 3 through 10.

Figure 3:
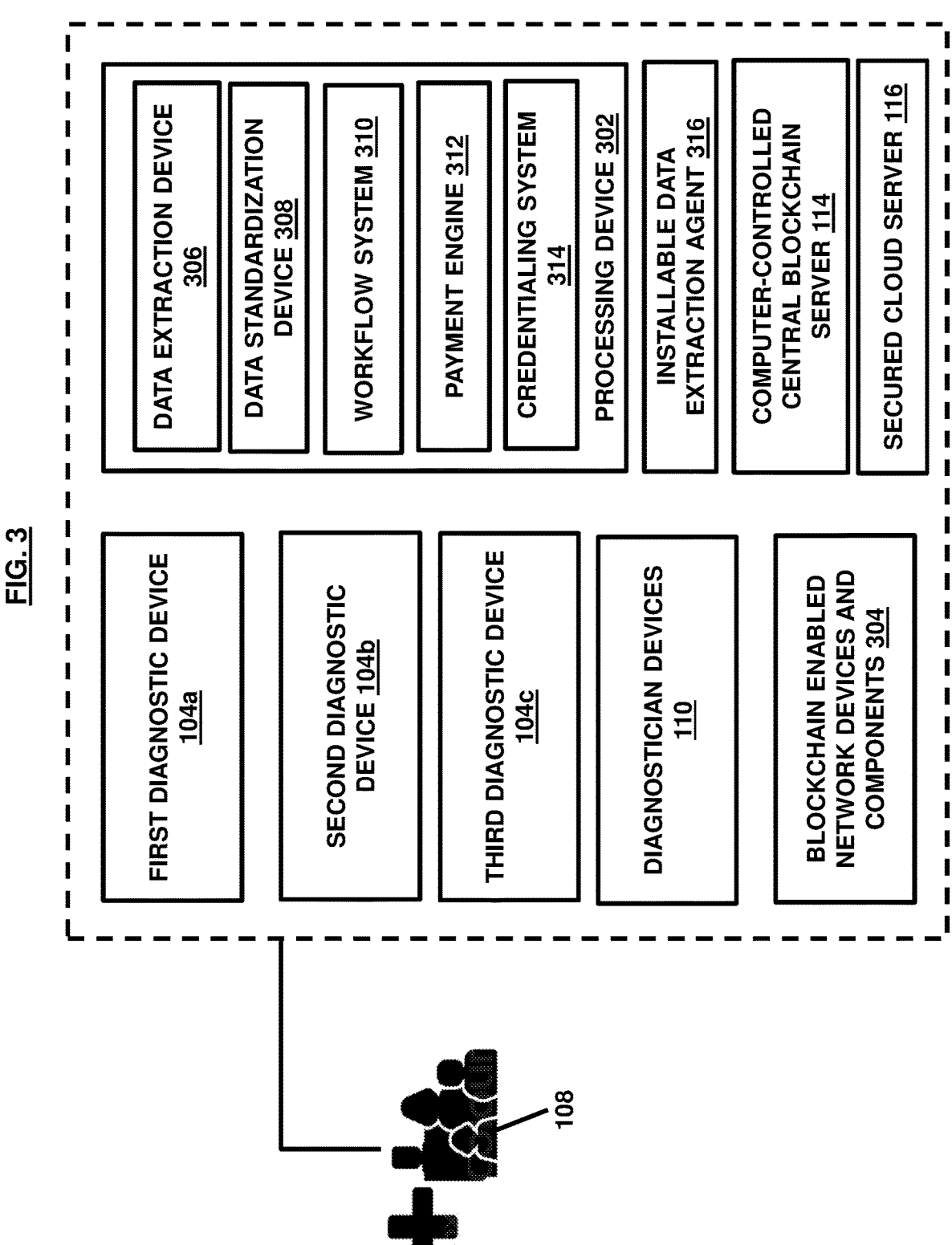
FIG. 3 illustrates, among other components, a processing device that may be coupled communicatively with a blockchain server and a secured cloud server, according to an embodiment herein.

FIG. 3, with reference to FIGS. 1 and 2, illustrates a processing device 302 that may be coupled communicatively with the blockchain server 114 and the secured cloud server 116. The processing device 302 and the blockchain server 114 may further be coupled to various blockchain-enabled network devices and components 304 to facilitate blockchain configured transactions.

The processing device 302 may include a data extraction device 306, a data standardization device 308, a workflow system 310, a payments engine 312, and a credentialing system 314. The processing device 302 and or the data extraction device 306 may be coupled to an installable data extraction agent 316 communicatively. These devices are discussed in further detail below.

Figure 4:
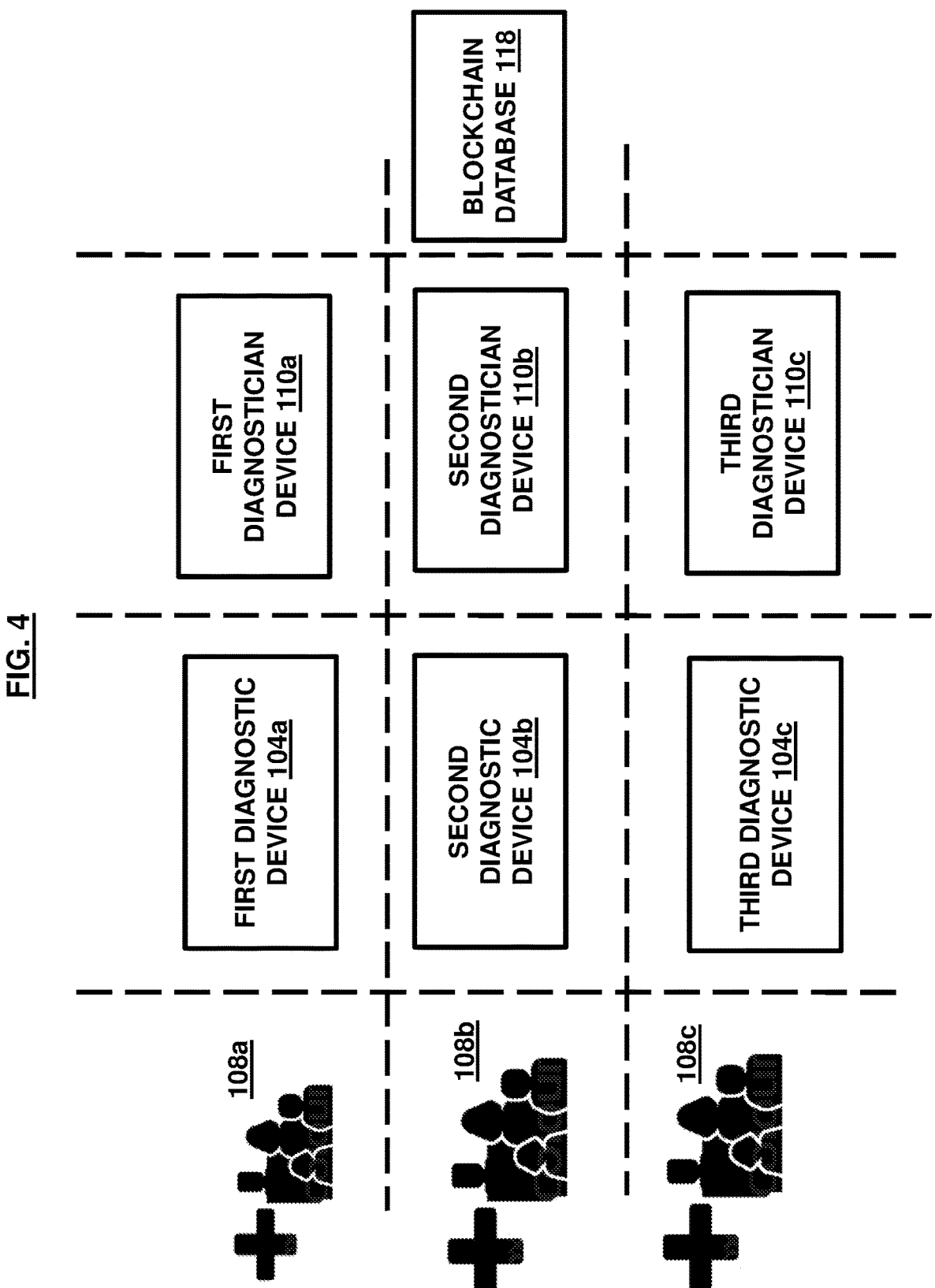
FIG. 4 illustrates distributed nature of a plurality of users within a diagnostic network according to an embodiment herein.

As shown in FIG. 4, with reference to FIGS. 1 through 3, the components in the architecture 100 or 200 operate in the form of discrete distributed layers. For example, the diagnostic devices 104 are located at a location remote from the location of the diagnostician devices 110. The diagnostic devices 104 are associated with the data sources 108 so that the diagnostic devices 104 may extract and retrieve the data or generate the data based on various parameters associated with the diagnostic devices 104. The diagnostic devices 104 can perform various diagnostic operations such as MRI, CT scan, X ray imaging etc. The diagnostician devices 112 on the other hand may be computer-enabled devices associated with the diagnosticians 110 to perform various tasks of managing, manipulating, and coordinating diagnostic tasks and to communicate with the blockchain server 114 and the cloud server 116 on behalf of the diagnosticians 110.

A blockchain database 118 shown in FIGS. 1 and 3 may be located at a location remote from the locations of the diagnostic devices 104 and the diagnostician devices 110. Additionally, one or more of the diagnostic devices 104 are located at remotely distributed locations. Similarly, one or more of the diagnostician devices 110 are located at remotely distributed locations. Each of the first diagnostic device 104*a*, the second diagnostic device 104*b*, and the third diagnostic device 104 are associated with entities such as the first data source 108*a*, the second data source 108*b*, and the third data source 108*c*. Each of these entities 108 may be proximately located to the respective diagnostic devices 104. In accordance with various embodiments, the various users in the diagnostic network 102 may be distributed physically at different locations. This may allow, for example, to generate diagnostic data contained in the plurality of computer-executable files at source locations where the diagnostic devices 104 are located. The computer-executable files containing the diagnostic data stored digitally may be read by the diagnostician devices 110 (associated with the diagnosticians 112) at different locations. The diagnostic data within the computer-executable files may be stored at altogether a different location such as within the blockchain database 118.

Referring now to FIG. 3 again, the processing device 302 is discussed herein. The processing device 302 may be configured as a special purpose processor to perform tasks in accordance with the various embodiments discussed herein. The data extraction device 306 may be configured to retrieve data from the diagnostic devices 104 and/or the diagnostician devices 110. For example, the diagnostic devices 104 may be associated with entities from whom the diagnostic devices 104 obtain digital data indicative of diagnostic parameters and respective values associated with individual entities. The obtained or retrieved data may be stored in the diagnostic devices 104 or separate storage devices coupled with the diagnostic devices 104. The obtained data from the entities such 108 may be unstructured, structured, or partially structured or a combination thereof. The structured data may represent data that has been organized into a formatted repository, such as a database, so that its elements can be made addressable for more effective processing and analysis. The unstructured data either does not have a pre-defined data model or is not organized in a pre-defined manner. The unstructured data may represent data that has not been organized into a formatted repository, such as a database, so that its elements cannot be made addressable for more effective processing and analysis. The partially structured data may represent data elements that contain a combination of the structured and unstructured data elements. For example, the first diagnostic device 104*a* may obtain data that is completely structured but in a first format. The second diagnostic device 104*b* may obtain data that is unstructured and in a second format. The data obtained by the third diagnostic device 104*c* may be in the form of partially structured data residing in a third format. Not only the structuring of the data in all the diagnostic devices 104 may be different but the format may also be different.

In accordance with various embodiments the diagnostic devices 104 may include devices such as electronic stethoscopes, sphygmomanometers, ophthalmoscopes, otoscopes, electrocardiographs, thermometers, magnetic resonance imaging (MM) devices, ultrasound devices, CT scan machines, laboratory equipment, devices for self-testing, in vitro diagnostic medical devices, X-ray equipment, screening devices, and the like. Each of these devices may be configured to be controlled through a computer and may contain or be coupled to a storage device and a transmitter for transmitting and receiving information from other devices within the diagnostic network 102.

The data extraction device 306 may extract entire or select data as required from the various diagnostic devices 104 that may be located at remote locations from the extraction device 306. The extraction device 306 may be communicatively connected with the diagnostic devices 104 over the diagnostic network 102 to facilitate transmission and receipt of the extracted data from the diagnostic devices 104.

As mentioned above, the diagnostic devices 104 may contain the data within the computer-executable files in different formats and structures. Therefore, the extracted data at the extraction device 306 may be unstructured or structured differently. The extraction device 306 may be coupled communicatively and/or operatively with the standardization device 308 that is configured to uniformly standardize the extracted data in accordance with the required standard such an HL7 standard.

The processing device 302 may contain the workflow system 310. In some embodiments, the processing device 302 may not include the workflow system 310 but may be separately coupled communicatively with the workflow system 310. The workflow system 310 may be configured to perform a set of tasks for managing certain computer-controlled tasks within the diagnostic network 102 among the various users and particularly among the diagnostician devices 104 and associated entities 108.

Figure 5:
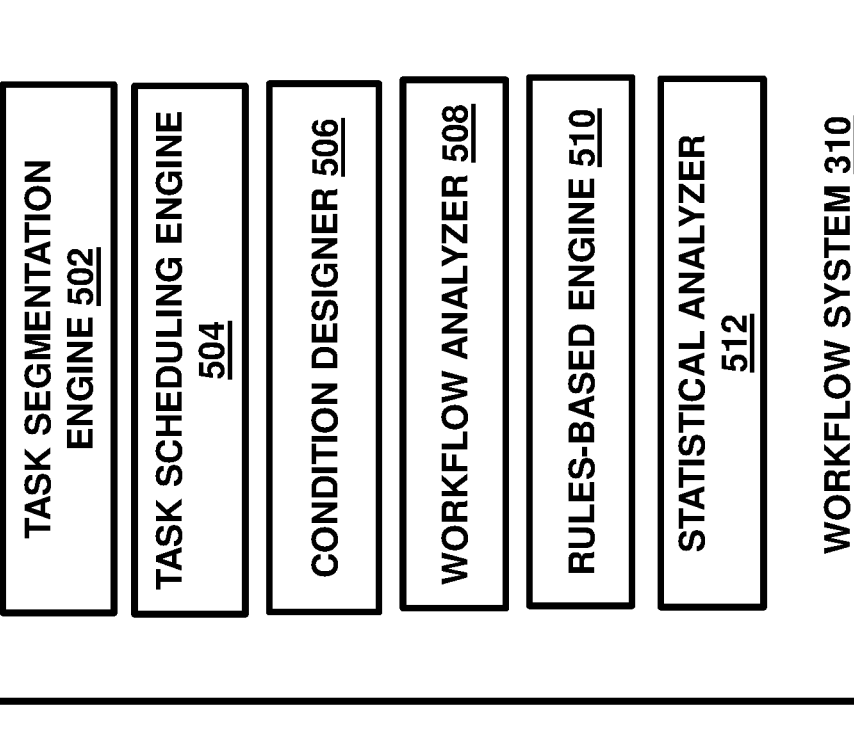
FIG. 5 illustrates an example of a workflow system according to an embodiment herein.

The various components of the workflow system 310 are illustrated in FIG. 5, with reference to FIGS. 1 through 4. The workflow system 310 is discussed herein in conjunction with FIGS. 3 and 5. The computer-controlled workflow system 310 or simply the workflow system 310 may include a task segmentation engine 502, a task scheduling engine 504, a condition designer 506, a workflow analyzer 508, and a rules-based engine 510. The task segmentation engine 502 may create one or more work flow steps for a set of tasks or workflow tasks defining a set of routing rules for one or more of the users that trigger or accept to execute a certain workflow task. For example, if a particular user agrees (as indicated through pre-registration or subscription settings) to read MRI images and prepare digital diagnostics using his/her associated diagnostician devices 110 controlled through a special purpose computer; the user may receive notifications over a graphical user interface of a display unit of the diagnostician device 110 or on another computing device. The notifications may relate to newly added workflow tasks about reading MM scans. The task segmentation engine 502 may present the work flow steps for each of the tasks that relate to reading of the MRI scans. The user can accept any of the tasks and accordingly corresponding workflow steps are presented to the user for executing the task. The workflow steps allow standardizing the process of executing a task by a plurality of users.

The task scheduling engine 504 opens up one or more tasks to the users based on their credentials and their preferences as indicative in their registered profiles. For example, a user may want to read only MRIs, another user may want to read MRIs as well as CT Scans, still another user may want to read diagnostic scans as well as also label or classify them to develop a structured taxonomy and definition for evolving AI. Two use cases are particularly discussed here for the workflow tasks. But more use cases may be applicable in accordance with various embodiments discussed herein.

In an example, the user may want to read diagnostic data related to brain scans. Whenever the workflow system 310 detects any task for reading a brain scan, the workflow system 310 presents the task for reading the brain scan contained within a computer-executable file to the user. There may, however, be more users as well within the diagnostic network 102 who may also access the computer-executable file for reading and who might have indicated their preferences for reading a brain scan. The task scheduling engine 504 ensures that whoever has better credentials is allocated the task, in an embodiment. In an embodiment, the task can be automatically allocated to whoever picks it the first. In an embodiment, if the reading is acceptable by more than one users, the task may be opened for even more than one user, though the condition within a marketplace such as payments may vary based on who accessed and accepted the task the first and who accepted it next and so on.

In some embodiments, the user may not wish to read a document such as a digitally captured brain scan, but may want to add labels to the document. In some embodiments, the user may want to add labels as well as perform reading of the digital document contained within the computer-executable file. Accordingly, conditions may be defined based on preferences of the user.

The labels or digital labels added by the user may serve to catalogue different types of documents or information within the diagnostic network 102 digitally and allow to perform artificial intelligence operations by identifying objects and elements of the information based on the labels provided by thousands or millions of the users within the network 102 which help recognition of the objects and information elements possible. Labeling can be performed by the users with their diagnostician devices 104 or with associated computing devices that are connected to the cloud server 116 and/or the blockchain server 114 which receives this labeled information in real-time and also utilize it for the purpose of artificial intelligence operations within the diagnostic network 102 such as for automated and intelligent reading of digital diagnostic documents contained within the computer-executable files.

The condition designer 506 defines and creates conditions as to who is allocated a workflow task. Conditions may be defined based on first come first served basis or based on credentials. Conditions may be defined based on preferences of the users or based on requirements. In some embodiments, the rules-based engine 510 may be provided to contain pre-stored and dynamically updating instructions that define how the conditions are defined. For example, the rules-based engine 510 may instruct credentials of a user to be set as high priority for allocating a task. The condition designer 506 may accordingly define specific conditions or exceptions about who should be permitted to view a task or accept a task for execution and so on. In some embodiments, the condition designer 506 may be contained within the rules-based engine 510.

The workflow analyzer 508 analyzes in real-time one or more workflow processes such as execution of the tasks by the users who are allocated a task or a plurality of users for whom the task is opened (which could be one or more users in the diagnostic network 102). In some embodiments, anyone can join or participate in the execution of a task such a reading of the diagnostic data or labeling it. The workflow analyzer 508 may include a statistical analyzer 512 to analyze workflow history of the workflow processes or tasks. The workflow analyzer 508 may calculate average processing time of each of the created workflow processes or tasks and also average processing time of similar tasks by a particular user. The workflow analyzer 508 may calculate daily load and global load associated with each user or with each task in the workflow system 310.

The workflow or task scheduling engine 504 and/or the tasks segmentation engine 502 may retrieve the tasks for allocation from the blockchain database 118 where the information gathered from the diagnostic devices 104 is stored and need to be executed through the workflow processes. The workflow scheduling engine 504 and/or the tasks segmentation engine 502 generates workflows that include steps for routing objects retrieved from an object repository contained within the blockchain database 118.

The workflow system 310 ensures that the information (each information element or extracted data piece referred to as an object alternatively) extracted from the diagnostic devices 104 and stored within the blockchain database 118 or the blockchain server 114 is processed for one of the various types of operations including diagnostic reading and labeling for AI, without limitations. Once the objects are read or labeled or processed for any type of operations, the objects along with the added information after the processing are stored within a separate database of the blockchain server 118 for subsequent use.

FIG. 6, with reference to FIGS. 1 through 5, illustrates various components of the data extraction device 306. The data extraction device 306 is discussed herein referring to the FIGS. 3 and 6. As discussed above in conjunction with FIG. 3, the data extraction device 306 may retrieve data in the form of the computer-executable files from the various diagnostic devices 104. In an embodiment, the data extraction device 306 may retrieve processed or executed workflow data from the diagnostician devices 110. Each of the first diagnostician, the second diagnostician, and the third diagnostician may be associated with their respective diagnostician devices 110 such as the first diagnostician device 110a, the second diagnostician device 110b, and the third diagnostician device 110c.

The data extraction device 306 may retrieve the computer-executable files from the diagnostic devices 104 and transfer them to the blockchain server. The data extraction device 306 may include capabilities to generate or retrieve data available in various formats. The data extraction device 306 may include an image recognition device 602 to extract image-based digital data, and a non-image based data extraction device 604 to capture data that is in other form such as in text format. The data extraction device 306 may include a visual display terminal 606 to present details about the extracted data or for allowing a user to interact with the data extraction device 306 through a graphical user interface enabled through the visual display terminal 606.

The image recognition device 602 may be coupled to or be contained within the data extraction device 306. The image recognition device 602 may include a communication interface 608 for establishing communication with various devices such as with the blockchain server 114 for automating transfer of the extracted data from the data extraction device 306 to the blockchain server 114, or with the diagnostic devices 104 or with the diagnostician devices 110.

The image recognition device 602 may include an image acquisition device 610 to receive signals containing image patterns and expressions and to read image-based data obtained from the diagnostician devices 110. The image acquisition device 610 may include or be coupled to a camera 612 for taking still or streaming images of the source data. The image acquisition device 610 may include a plurality of multichannel amplifiers (MCA) 614 such that each amplifier of the multichannel amplifiers 614 may be defined to receive a specific type of sensed information from a particular type of sensor or camera 612 sourcing signals for the image recognition device 602. The amplified signals obtained from the plurality of multichannel amplifiers 614 may then be transmitted to an image segmentation device (ISD) 616 for fragmenting the received image patterns to process reading of the data. These federated image patterns may then be transmitted to a microcontroller 618 for further processing. The image acquisition device 610 may be adapted to receive the digital audio signal and generate/transmit the audio signal to the microcontroller 618 for image recognition and data reading. The image recognition device 602 may be adapted to sample an analog signal to generate the digital audio signal and interface with the microcontroller 618. The microcontroller 618, in association with necessary recognition software 620, may be adapted to discriminate between multiple image patterns to output a stream signal. The stream signal represents image-based source information read by the data extraction device.

The non-image based data extraction device 604 may be configured to read a plurality of texts in different formats such as numerical data, text information written in a variety of languages etc. The non-image based data extraction device 604 may include a language translator to translate the language of the source data into a standard language that is maintained within the blockchain server 112.

FIG. 7, with reference to FIGS. 1 through 6, illustrates the various blockchain-enabled network devices and components 304 without limitations. The blockchain-enabled network devices and components 304 are discussed herein with reference to FIGS. 3 and 7.

The blockchain-enabled network devices and components 304 include a blockchain device 702. The blockchain device 702 may include a processing device 704 and a transmitting device 706 that each is capable of blockchain integration unlike generic devices. The processing device 704 may process all blockchain tasks through computer-controlled software and hardware tools. The transmitting device 706 can allow transmission of information such as the computer-executable files from the blockchain server 114 to the cloud server 116 or to any of the users and their respective associated devices as allowed within the diagnostic network 102 based on permissions and access rights. The transmitting device 706 may also enable various types of communication with other systems within the diagnostic network 102.

The blockchain device 702 also includes hardware 708. The hardware 708 may comprise a specific blockchain-enabled server device 710 and a smart device 712 running a specific dedicated software application operated by a user. The smart device 712 is configured to engage in specific communication with the blockchain-enabled server device 710. The smart device 712 is configured to receive inputs from a user and generate transaction identifiers based on the received inputs such that the transaction identifiers enable processing and generating of smart contracts 714 within the blockchain. The smart contracts 714 cannot be tempered and provide security from any sort of vulnerability within the blockchain. The smart device 712 may be coupled to a user interface that allows the user to input details.

The blockchain-enabled server device 710 performs tasks enabling communication with the smart device 712. The blockchain-enabled server device 710 further performs at least one of these tasks: storage of at least one database or a portion thereof and/or data for placement therein in the blockchain database 118, access the at least one database including the blockchain database 118, update the at least one database including the blockchain database 118, allow the smart device 712 to access and receive information in whole or in part from the at least one database. In some embodiments, the at least one database such as the blockchain database 118 may contain at least one unique hash, at least one timestamp of the at least one unique hash, and/or other data for generating the smart contracts 714.

The transmitting device 706 may allow transmission of at least one hash file and/or hash blockchain to the blockchain-enabled server device 710. The transmitting device 706 may further allow receiving a transaction confirmation and/or identifier from the smart device 712, creating a hash file and/or hash blockchain from the digital data and/or digital content, receiving the hash file and/or hash blockchain and the timestamp from the smart device 712. The processing device 704 may compare the hash file and/or hash blockchain to other verification information for verifying authenticity of a variety of information.

The processing device 704 may generate a network identifier 716, a transaction identifier 718, and a blockchain address identifier 720 to specify a particular transaction that involves such as receipt of a service associated with the diagnostician devices 110 (such as read service or a label service as discussed above), enabling a payment corresponding to a service, submitting a workflow task, receiving responses for a particular workflow task and other types of transactions within the diagnostic network 102. Each set of identifiers define a specific transaction indicated through a digital contract such as a smart contract 714 and cannot be tempered. The smart contract 714 allows tracing evidences of the transactions for any particular task in the diagnostic network 102. In an embodiment, the processing device 704 is configured to cause the smart contract 714 to be generated based on the network identifier 716, transaction identifier 718, and the blockchain address identifier 720 such that the smart contract 714 is configured to automatically validate a transaction using a special key associated with a user or a transaction.

A transaction message 722 may be generated by the processing device 704 to inform respective users. In an embodiment, the transaction message 722 may be associated with one or more secured hash links so that the transaction message is generated when the one or more secured hash links are activated.

The processing device 704 may generate the network identifier 716 that may be associated with the blockchain network 102 and the transaction ID (identifier) 718. The processing device 704 may generate the blockchain address identifier 720 using at least a unique key and one or more hashing codes associated with the respective diagnostician devices 110 and/or the diagnostic devices 104.

In an embodiment, the blockchain address identifier 720 may be based on a public key corresponding to a private key that was used to register the transaction on the blockchain such that the public key and the private key are part of a public/private key pair associated with the transaction indicative of the execution of a particular workflow task by a diagnostician or any other user within the diagnostic network 102.

In an embodiment, the processing device 704 may generate the transaction message 722 based on one or more standards and includes a plurality of data elements, including at least a first data element configured to store a proof of transaction as the evidence reserved for private use upon request for verification by respective associated users. The use of evidence privately is indicative of a controlled and secured access of the evidence only to authorized users.

The blockchain device 702 may include or is coupled to a rules engine 724 that defines and facilitates processing of a set of computer-executable rules defining instructions for verification of identity information of the diagnostician devices 110 and the associated diagnosticians 112 and for reviewing and verifying the extracted data that has been processed through one or more of the various types of tasks including the reading and labelling, without limitations. The computer-executable rules may allow verifying proof of execution based on the occurrence of a transaction, receipt of digitally executable location information, receipt of digitally executable voice input, or receipt of digitally executable image input, etc. from the diagnostician devices 110 who submit (or is automatically extracted by the extraction device 306) a response indicative of execution of the workflow task along with the extracted data corresponding to the workflow task from the diagnostician devices 110 that eventually get stored in the blockchain database 118.

The rules engine 724 may include or be coupled to a memory circuit, a processing circuit, integrated circuits, chipsets, and rules translators (not shown). The blockchain device 702 and the blockchain server 114 may be coupled to a central verification device 726 shown in FIG. 7 that may also be coupled communicatively to the cloud server 116.

The central verification device 726 is configured to verify identity information of the user in the diagnostic network 102 who requests to access the workflow task for execution. The verification performed by the central verification device 726 allows to determine the identity of the user accessing the workflow task.

The central verification device 726 may allow comparing pre-stored registered and/or identity information about the user as stored in the blockchain database 118 with external information received from the user during the access to verify whether the user is a genuine user registered with the system and represents the same actual user.

The central verification device 726 may include or is coupled to the rules engine 724 that defines and facilitates processing of a set of computer-executable rules defining instructions for verification of the identity information. The computer-executable rules may allow verifying proof of identity based on pre-registered information and real-time information such as occurrence of an event, receipt of digitally executable location information from the user, receipt of digitally executable voice input from the user, or receipt of digitally executable image input from the user and the like.

Based on a digital output generated by the central verification device 726 indicative of identity verification of the diagnostician device such as 110a, the central verification device 726 processes or rejects a request by the user to access a particular workflow task in accordance with a set of predefined computer-executable rules. The identity information may be linked with credentialing information of the user so that the capabilities and preferences of the user may be assessed from the identity information in order to allocate the workflow task to the user associated with the diagnostician device 110a.

The rules engine 714 includes at least one rule that allows identifying the user and verification information of the user to grant or reject the access. The blockchain device 702 may be accessed through an interactive graphical user interface 728 for interactions and engagement.

Figure 8:
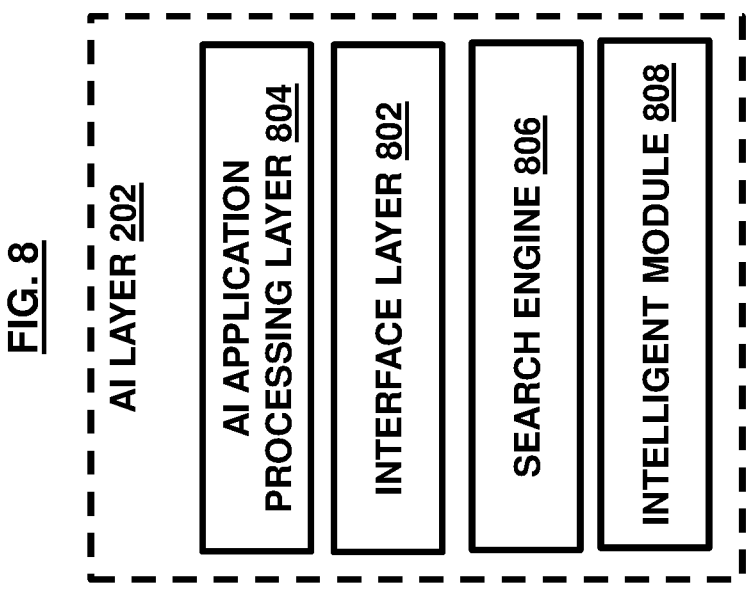
FIG. 8 illustrates an example of an AI system that may be integrated within a blockchain server to enable the artificially intelligent diagnostic network in accordance with an embodiment herein.

FIG. 8, with reference to FIGS. 1 through 7, illustrates the AI layer 202 (shown in FIGS. 2 and 8) that may be integrated within the blockchain server 114 to enable the artificially intelligent diagnostic network 102 in accordance with the embodiment illustrated in FIG. 2.

The AI layer 202 or AI system 202 may include an interface layer 802 to receive inputs form a user or an external system or an internal system that serves as an initial input to the AI layer 202. The interface layer 802 analyzes the initial inputs, ask questions to clarify the inputs or to get more inputs, request user feedback to proceed on further analysis, and examine whether enough details are available to proceed. The user herein with respect to AI layer 202 may indicate automated systems that provide the extracted data to the blockchain server 114 or an administrator who manages the blockchain server 114 or the cloud server 116 or the extraction device 306 itself or the users such as the diagnosticians 112 and their associated devices 110 that submit data to the blockchain database 118. In an embodiment, the labels that are digitally added on the diagnostic data generated by the diagnostic devices 110 and stored in the form of the computer-executable files by the diagnosticians 112 may be used as the initial inputs for the AI layer 202. As more and more diagnosticians 112 read more of the data obtained from the diagnostic devices 104 and label them, the better the initial inputs become and the capabilities of the AI layer 202 improve accordingly.

The AI layer 202 further includes an AI application processing layer 804. The AI application processing layer 804 collects the initial inputs and related information from internal databases such as the blockchain database 118 and external Internet sources, and process the information, make analysis and judgment for automated reading of the diagnostic data extracted from the diagnostic devices 104. This allows automated reading of the diagnostic data as opposed to the reading by the diagnosticians 112 associated with the diagnostician devices 110. After the AI system 202 achieves optimal improvements with gradual evolution of the initial inputs, the processing by the AI layer 202 may become intelligent enough to be relied upon and delivered from the system to end users as final output to assess reading or evaluation of their diagnostic reports and digital data.

The AI layer 202 may include a search engine 806 that runs intelligent information searching and mining for complicated phrases or sentences to search for the related information to improve the initial inputs.

The AI layer 202 may include an intelligent module 808 that collects, analyzes, and judges the relative information and the initial inputs to find the most appropriate ways to evolve the AI layer 202 and the initial inputs. The intelligent module 808 may also analyze thoughts input, which could be in the form of voice, images, alphabet, words, string, or various ways of human perception that can be translated into data, and think on user's behalf to produce clarified, concrete and specific objectives through intelligent algorithms and operations.

Thus, an advanced intelligent application system is provided, where based on the initial inputs as aggregated from the internet searches, manual inputs and the labels added by the users, and the continuous interface/communication (hint, question/answer for clarification, detailed categorizations, analysis etc) between the system and the users and administrator, the application runs through its intelligent algorithm to clarify and read the diagnostic data extracted from the diagnostic devices 112 directly, find the most appropriate answer and reading for the extracted data, and do much more operations including the execution of the various workflow tasks in an automated way.

Referring now to FIG. 3, the processing device 302 may include the payment engine 312 that may facilitate monetary transactions digitally for the users based on the execution of the workflow tasks as scheduled by the workflow system 310. The payment engine 312 may be coupled to an electronic device or the blockchain server 114 accessible to the electronic device so that the payment engine 312 may receive the request from the electronic device about payments for the users executing the workflow tasks. The electronic device may be a mobile device configured to approve payment transactions for the payment engine 312 to execute a set of rules that define payment terms and processes and accordingly make payments to the users as appropriate. The payment engine 312 may allow a plurality of payments methods to be available for the users in response to the payment request from the users or automatically based on the completion of the workflow tasks and approval from the electronic device or internal systems and based on payment evaluation criteria. The payment engine 312 may consider user-defined criteria for payment methods such as including information related to user preferences with respect to the payment methods and criteria related to terms associated with the plurality of payment methods as saved in the blockchain server 114. The payment engine 312 along with other components such as the extraction device 306, workflow system 310, blockchain server 114, cloud server 116, and the various users and their associated devices may enable a computer-controlled diagnostic marketplace or simply a computer-controlled marketplace, for enabling various transactions within the diagnostic network 102.

The installable data extraction agent 316 may be associated with the diagnostic devices 110 that are connected within the diagnostic network 102. The installable data extraction agent 316 may be deployed within the diagnostic devices 110 or may be coupled to the diagnostic devices 110 separately to allow extraction of the data from the diagnostic devices 110 by the extraction device 306 from a remote location within the diagnostic network 102.

The processing device 302 may be communicatively coupled to a credentialing system 314. The credentialing system 314 is configured to manage and verify credentials of the users participating in the marketplace for executing one or more of the workflow tasks including such as reading of the data contained in the computer-executable files indicative of the diagnostic data acquired from the diagnostic devices 104 and standardized accordingly and/or labeling of the data without limitations. An exemplary credentialing system 314 is show in FIG. 9.

Figure 9:
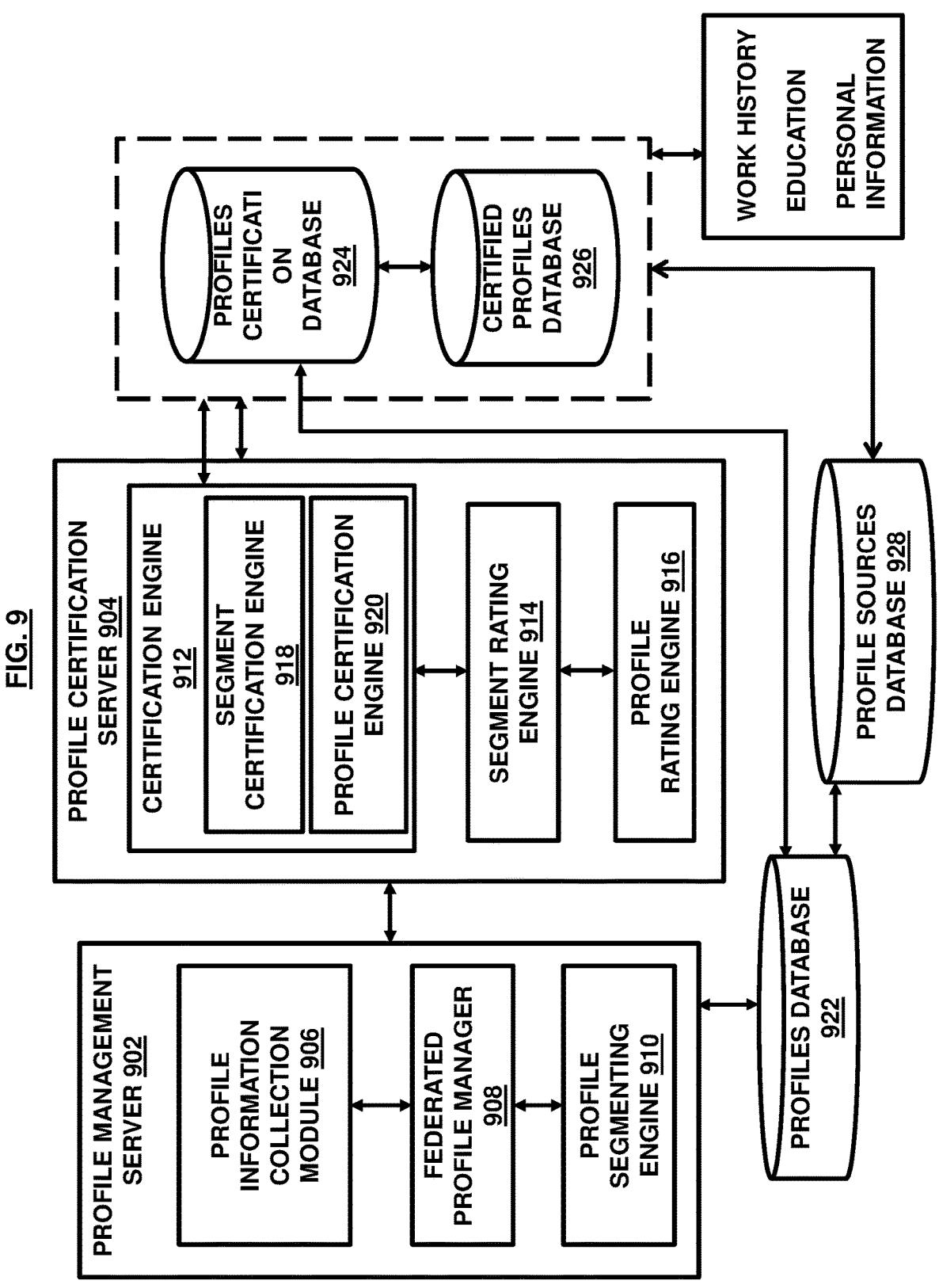
FIG. 9 illustrates an example of a credentialing system in accordance with an embodiment herein.

FIG. 9, with reference to FIGS. 1 through 8, illustrates the credentialing system 314 in accordance with an embodiment. As shown, the system 314 may include a profile management server 902 and a profile certification server 904. The profile management server 902 includes a profile information collection module 906, a federated profile manager 908, and a profile segmenting engine 910.

The profile information collection module 906 may be configured to generate information about the plurality of users. In some embodiments, the profile information collection module 906 can be disposed separately from the federated profile manager 908; while in other embodiments it can be included in or coupled to the federated profile manager 908. The profile information pertaining to profiles of the plurality of users can be generated by distributing application forms through a graphical user interface accessible by the users such that the users can fill the forms and submit with the system digitally. The information can be transformed in the form of profiles by the federated profile manager 908. The segmenting engine 910 may then use the profiles information and perform the task of segmenting of the common profiles into the federated profiles associated with each of the users.

The profile certification server 904 may be communicatively coupled to or included in the profile management server 902. The profile certification server 904 may include the certification engine 912, a segment rating engine 914, and a profile rating engine 916. The certification engine 912 may further include a segment certification engine 918 and a profile certification engine 920.

The segment certification engine 918 may be configured to facilitate credentialing or certification of the federated profiles associated with their common profiles (non-segmented full profiles) associated with each of the users. The segment certification engine 918 is configured to allow a plurality of crowdsourced respondents to respond to the federated profiles associated with the common profiles of the plurality of users and credential them. The credentialing of each of the federated profiles associated with the common profiles of each of the users contributes to credentialing of the entire common profile of the users upon collation of the credentialed federated profiles. As more and more persons or respondents from the plurality of crowdsourced respondents verify the information in the federated profiles, the trust associated with credentialing of the respective federated profiles increases. Therefore, the crowdsourcing may allow credentialing of the federated profiles to a higher degree of accuracy and reliability. Since the discrete federated profiles associated with a user are credentialed from the plurality of crowdsourced respondents, the credentialing defines a high level of accuracy and may be considered as highly authentic and reliable and acceptable by third parties or agencies.

The segment certification engine 918 is adapted to certify the stored federated profiles relating to the users who must have their credentials verified for use by the blockchain server 114 before allocating any workflow tasks in the diagnostic network 102 so that credentialing of the profiles ensures right capabilities and trustworthiness and recognition of the users.

According to some embodiments herein, a number of sources credentialing a particular federated profile may be associated with each of the segments to indicate a level of accuracy of the credentialing information. Also, the relevant information about credentialing such as who credentialed, when credentialed may also be associated with each credentialing of each of the federated profiles so that an authenticity may be judged by associating an overall impact of the federated profiles' credentialing, number of times credentialed, and trust factor about the source who verified and relevance about the source and time when verified. Therefore, in such embodiments, a multi-scaled and cumulative score may be determined, and multi-scaled and cumulative credentialing may be performed based on the multi-scaled cumulative score determined to provide a higher value of trust and reliability when such users join the diagnostic network 102 for reading and labeling digitally and other workflow tasks in the diagnostic network 102.

The information pertaining to credentialing of the individual federated profiles of a particular common profile associated with a user may influence an overall credentialing of the common profile or entire profile. For example, the individual credentialing of the federated segments may contribute to the overall common profile credentialing such that the credentialing of the overall common profile may depend on each of the federated profiles' credentialing with a weightage attached to each credentialing of the federated profiles. The collated contribution considering weightage effect of each credentialing finally decides credentialing of the overall common profile. The task of credentialing the overall common profile associated with a user may be performed by the profile certification engine 920. For example, the profile certification engine 920 may facilitate credentialing of the profile in entirety based on the collated effect of credentialing of the federated profiles associated with the common profile of the user. The profile certification engine 920 may receive information pertinent to credentialing of each of the federated profiles associated with a common profile and then associate the defined weightages to each of the federated profiles and perform cumulative credentialing of the common profile. In an embodiment, the weightages may be determined based on parameters defined by the workflow system 310. In such embodiments, the weightages may be defined based on for example past experiences or current understanding about importance of accuracy of credentialing for different segments. For example, the accuracy of credentialing may be more important for work history than information pertinent to hobbies of a user when applying for a workflow task. Therefore, the objective use of the credentialing information may influence determination of the weightages and hence the overall credentialing. Therefore, a score indicative of the influence of the objective may be associated for the credentialing purposes in some embodiments. In some embodiments, the profile certification engine 920 may perform credentialing of the common profile in a custom defined manner and also in association with the objective score as required by the workflow system 310.

The profile certification server 904 further includes the segment rating engine 914. The segment rating engine 914 is configured to associate a rating to each of the credentialed federated profiles based on credentialing from the crowdsourced plurality of respondents and depending on a level of accuracy and trust associated with the credentialing of the federated profiles of the diagnosticians 112. The rating may depend on who credentialed a federated profile, when was a profile credentialed, how many times a profile was credentialed, how many unique credentials are done, relevance of the respondents credentialing the federated profile, relationship of the respondents with the user of the credentialed federated profile, and the like.

The profile certification server 904 may further include the profile rating engine 916. The profile rating engine 916 is configured to associate a rating to an entire profile based on credentialing of each of the federated profiles and ratings associated with each of the federated profiles as determined by the segment rating engine 914 cumulatively.

The profile management server 902 is coupled to a profiles database 922 to store information pertinent to the profiles of the plurality of users. The profiles database 922 may be coupled to the federated profile manager 908 such that the federated profile manager 908 maintains the information stored in the profiles database 922.

The profile certification server 904 may be coupled to a profiles certification database 924. The profiles certification database 924 is configured to store information pertinent to credentialing such as certification status of the federated or common profiles associated with the plurality of users. For example, the certification status may include one or more of a verified segment, verified profile, pending verification, verification in progress, segment rejected as incorrect, profile rejected as incorrect and the like. The profiles certification database 924 may be coupled to the profiles database 922 and the certification engine 912.

The profile certification server 904 may be coupled to a certified profiles database 926. The certified profiles database 926 may further be coupled the profiles certification database 924. The certified profiles database 926 may be configured to store profiles that have been verified by the certification engine 912. An authorized entity such as the blockchain server 114 may be allowed a direct access to the certified profiles database 926 based on certain defined preferences and rules. The certified credentialed profiles database 926 may further store information pertinent to one or more of work history, education, and personal demographics, affiliations to institutes etc of one or more users corresponding to one or more of verified profiles.

The profiles database 922, profiles certification database 924, and the certified profiles database 926 may be coupled to a profiles sources database 928. The profile sources database 928 may include information about a plurality of sources in the crowdsourced network that are linked to the federated profiles associated with the plurality of the users, and information about a plurality of sources who responds to the federated profiles for credentialing. For example, in the crowdsourced network, the plurality of respondents may credential the federated profiles and thus the profiles sources database 128 may store their details, their names, other information, their relevance and relationship with the users associated with the federated profiles they credential and time of credentialing, and location of original credentialing or any other such information pertinent to the credentialing sources etc.

Figure 10:
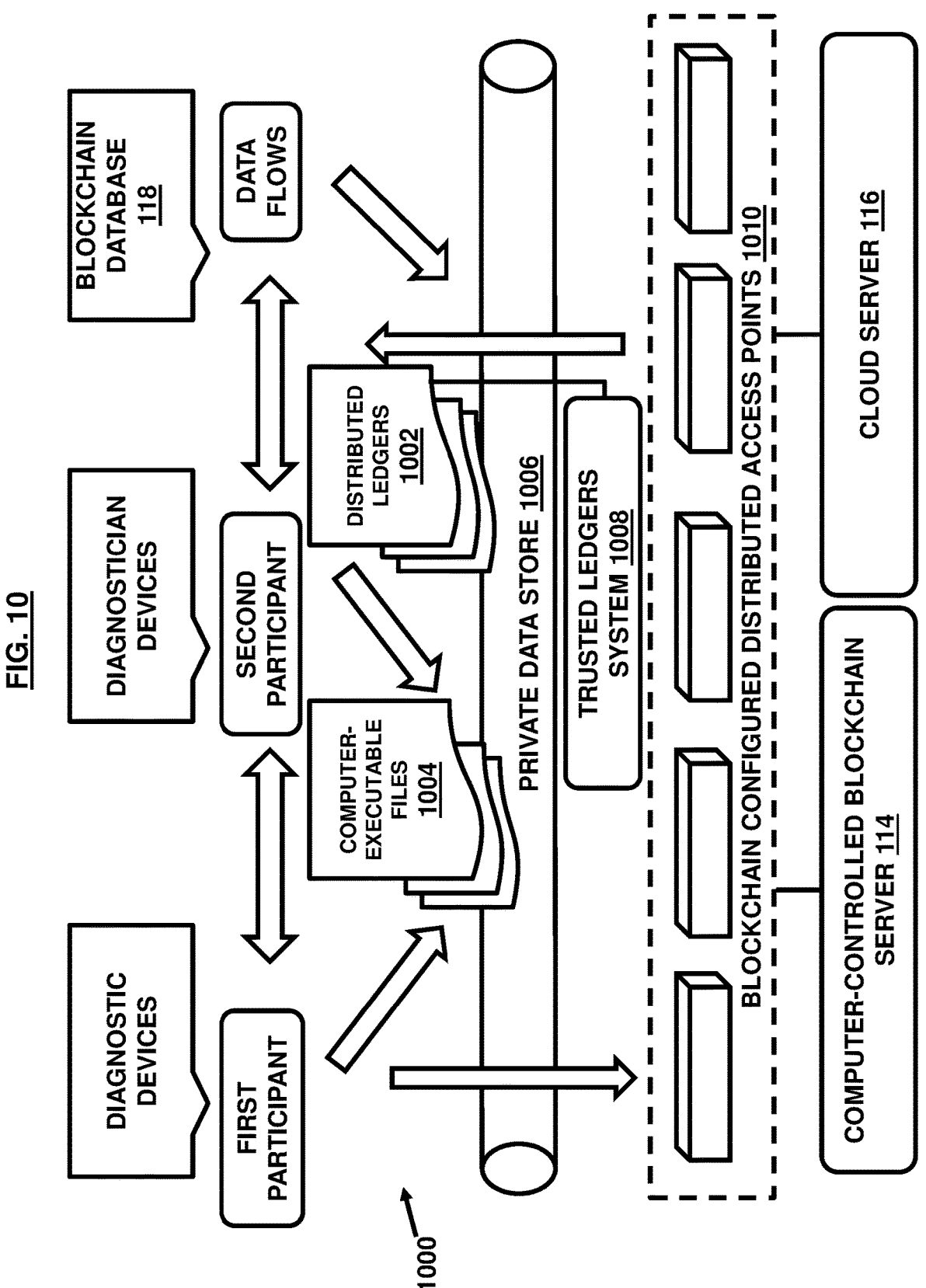
FIG. 10 illustrates an exemplary blockchain configured ecosystem architecture in accordance with an embodiment herein.

FIG. 10, with reference to FIGS. 1 through 9, illustrates an exemplary blockchain configured ecosystem architecture 1000 containing one or more components of the system as discussed in conjunction with FIGS. 1 and 2 and also contains additional components so as to allow integrity of submission of the workflow documents, processes, the computer-executable files and the like. This may facilitate association of an identity to the responses and workflow tasks thus submitted and executed by the users and also define and store a geographical and temporal identity such as when and in which location presence of the users and their respective devices such as mobile communication device, computing device, the diagnostician devices 110, and the diagnostic devices 104 are noted. The blockchain configured ecosystem architecture 1000 may provide a crowdsourced integrity network for storing the workflow tasks and documents and the computer-executable files containing the workflow documents without limitations instead of locally stored information by the different users that may be tempered.

The ecosystem architecture 1000 may be blockchain configured involving various blockchain devices. For example, the computer-controlled blockchain server 114 and the cloud server 116 that may interact with the blockchain device 702 and the various users and store the computer-executable files may be blockchain configured. A network that facilitates interaction across all components may be a blockchain integrity network. The blockchain network 102 may build trust among the various users or entities and their associated computing terminals or devices or diagnostician devices 110 even if the devices/terminals etc may not know one another. The blockchain network 102 may allow connections and transactions and recording and sharing of the workflow tasks and the computer-executable files in a trusted mode. A record of transactions and sharing and data from various terminals/devices stored on the blockchain in the form of computer-executable distributed ledgers 1002 may provide proof to command the necessary trust among the terminals/devices (such as those associated with various users including the diagnostician devices 102 to cooperate through a peer-to-peer or peer-to-client distributed digital ledger technology. The ecosystem architecture 1000 may include a distributed trusted ledgers system 1008 containing the distributed blockchain ledgers 1002 associated with a plurality of computing terminals and devices such that each ledger stores a copy of the computer-executable files such as 1004 shown in FIG. 10 or the workflow documents or the workflow tasks and the trust notes for defining security and trust among the computing terminals and devices across the network 102 so that each computing terminal trusts the other computing terminal through the blockchain. The distributed ledgers system enables coding of rules-based contracts that execute when specified conditions are met. The distributed ledgers 1002 make it easier to create cost-efficient networks where any device or any task associated with a task allocation or delivery or task execution may be tracked, without requiring a central point of control.

The various computing terminals or devices in the network serve as distributed peer-to-peer nodes and connections. The blockchain server 114 may serve as a client device configured to perform the task of validating and verifying various types of information including the extracted data and the workflow processes and the profiles of the users based on the rules as defined. Each terminal/device/node in the ecosystem architecture 1000, etc. may get a copy of the blockchain which may get downloaded automatically upon joining the blockchain integrity network 102. Every node or the device in the network 102 is an administrator of the blockchain, and may join the network 102 voluntarily so that the network 102 is decentralized.

The blockchain may eliminate the risks that come with data being held centrally by storing data across the network 102 which may include the computer-executable files 1004 containing the extracted data and the workflow documents. The blockchain security may use encryption technology and validation mechanisms for security and integrity verification. The security may be enabled through public and private keys. A public key may define a user's address on the blockchain. The private key may give its owner an access to various digital assets in the network 102.

In an embodiment, the distributed ledgers 1002 may enable coding of the smart contracts will execute when specified conditions are met. These smart contracts may protect the information associated with the workflow tasks and the extracted data and eliminate the risk of the computer-executable files 1004 copying and redistribution without protecting privacy rights.

The blockchain configured ecosystem architecture 1000 may provide a private view for the various devices and the entities operating in the network 102 through a private data store 1006 so that each such device may privately access the computer-executable files 1004 based on various policies such as based on their respective identities. Each of the devices may access the computer-executable files 1004 through the dedicated private store 1006 available through the plurality of distributed blockchain configured access points 1010 which may be enabled in the form of distributed blocks as shown in FIG. 10, with each block providing a facility to access the features of the blockchain configured ecosystem architecture 1000 by different terminals and devices at the same time based on defined and granted access rights.

The private data store 1006 may provide a virtual storage to facilitate interaction, information exchange, reviewing, and presentation of the computer-executable files 1004. For example, the private data store 1006 may allow a virtual storage and presentation of only limited executable files 1004 or portions of the executable files 1004 for access by particular nodes in accordance with permissions granted for reviewing. The private data store 1006 may be configured to auto-hash review interactions at any required interval. This compartmentalization of the computer-executable files 1004 ensures that the computer-executable files 1004 are secured and private as per access rights authorized to the nodes. The data presented on the private data store 1006 of the blockchain serves as a secure way to ensure that the private data store 1006 is in sync with any permissioned access.

In an embodiment, the blockchain configured digital ecosystem architecture 1000 may provide a federated blockchain comprising of several entities/users such as the diagnostic device 102*a*, diagnostician device 110*a*, diagnostician device 110*b*, and their associated computers and devices and sensors and their associated entities that jointly interact to process transfers of data through a trusted, secured and distributed network of the blockchain configured access points 1010.

The embodiments disclosed above allow to create a blockchain based diagnostic network. Entities can therefore manage their diagnostic devices and diagnosticians easily. The architecture discussed herein allows separating diagnosticians, diagnostic devices and the network that stores data. The architecture disclosed herein allows a diagnostician such as a radiologist or a lab technician or anyone who deals with data to access the network and act as a user. It separates a diagnostic device form its digital data and put that on blockchain and it does not matter where the data is placed. The diagnosticians and their associated devices can be made available in the architecture framework in the form of a marketplace. For example, if someone gets an MM performed at a local facility, the location of the person who reads it should not matter. The system knows how to retrieve digital diagnostics from its resource.

The architecture and the system discussed herein allow separating the diagnostic devices from data which is separated from experts. This makes it possible to remove the expert layer and replace it with AI at some point in time. Once the data is on the network then the diagnosticians can do reverse auction and say whenever an MRI for example is available in a particular location, they would want to do a read on it. They can pull it and do the read, annotate reporting etc on the network. Then it goes back to the device where the data is collected and associated authorized persons. Whoever does the first read is paid the most. Second and subsequent leads can be paid less. Experts can be offered additional money if they did other tasks such as labels for AI. The system allows people and devices to register themselves on the network as experts for different kinds of machines.

The disclosed system herein allows separating of the digitally configured diagnostic devices 104 and the diagnostician devices 110 associated with respective users to facilitate their remote-based integration within the computer-controlled ecosystem 100 or 200 as shown in FIGS. 1 and 2. The remote-based integration also referred to as tele-diagnostics or remote-based diagnostics allows to perform a series of computer-controlled tasks that are otherwise possible only in a physically unified setup and that too with limited privacy and is vulnerable and insecure. Further, the various systems, components and devices as discussed herein are configured in a blockchain setup to ensure data flowing across the devices 104 and 110 and associated users is not tempered in any form. The remote-based or tele-diagnostics within the blockchain configuration allows an infrastructure for the integration of thousands or tens of thousands of or even more digitally configured devices to perform controlled tasks and operate in a secured framework that is not vulnerable and where the stored data remains unchanged in a digitally secured manner through a method that allows configuring multiple copies over the blockchain that cannot be tempered.

The blockchain configured server 114 receives the digital information in the form of the computer-executable files from the diagnostic devices 104 and the diagnostician devices 110. The diagnostic devices 104 send the information that is generated from the data sources 108 in a digital format. The diagnostician devices 110 send the respective information to the blockchain configured server 114, wherein the sent information is generated after processing the workflow tasks through a computer-controlled system using inputs from the information received from the diagnostic devices 104 through the blockchain configured server 114.

In embodiments, the blockchain configured server 114 processes the information received from the diagnostic devices 104 and the diagnostician devices 110 to produce an output that involves transformation of certain inputs including a set of computer rules and the information received from the diagnostic devices 108 and the diagnostician devices 110. The output is further processed to involve creating a set of copies of the data contained in the form of computer-executable and blockchain-executable files that are retained in the form of blocks over the blockchain which are accessible through a plurality of access points as discussed above. No single entity has dominion over the data stored in the blockchain including these blockchain executable files processed by the blockchain device 702. It is a single recorded instance of the transaction distributed across parties with varying permission levels. If a disaster strikes one node or connection, it does not change or lose the record, as it still remains in its single, unaltered state across remaining nodes, thereby proving enhanced scalability and protection to the data distributed and used across the network among the wide base of users without any sort of interruption. In some embodiments, for each operation of the blockchain by the blockchain device 702 for converting the inputs into the desired output, the blockchain device 702 and or the various systems communicatively coupled with or included within the blockchain device 702 generate an identifier using at least a public key included in a transaction request and one or more hashing and/or encoding algorithms as discussed above to verify the identity of users involved within the transaction.

In addition to the features described above, the ecosystem 100, 200 and various components and systems contained therein provide several enhancements over the conventional solutions. The computer-controlled blockchain server 114 allows improved data storage and retrieval methods with significant improvements over conventional storage and data access systems. The blockchain server 114 is capable of interacting with the blockchain-enabled network devices and components 304 in the network 102. Any data stored within or through the blockchain server 114 or within devices and databases that are communicatively coupled to the blockchain server 114 such as the blockchain database 118 allow secured retrieval, storage, and access of any type of information stored or to be stored therein through secured authentication mechanisms by performing a set of blockchain specific transaction identification tasks including such as creating the hash file and/or hash blockchain from the digital data and/or digital content and receiving the hash file and/or hash blockchain and the timestamp from the smart device 712 as discussed above further in conjunction with FIG. 7.

The processing device 704 may further store a proof of transaction as evidence reserved for private use upon a request for verification by a respective associated user. The use of evidence privately is indicative of a controlled and secured access of the evidence only to authorized users. The evidence cannot be tempered because of the very nature of blockchain capabilities that stored multiple replica of the same information in a secured distributed mode.

The data collected from the devices 104, 110 and associated users cannot be tempered in any form when stored in the blockchain database 118 and/or the blockchain server 114. The server 114 configuration allows an infrastructure for the integration of thousands or tens of thousands of or even more digitally configured devices to perform controlled tasks and operate in a secured framework that is not vulnerable and where the stored data remains unchanged in a digitally secured manner through a method that allows configuring multiple copies over the blockchain that cannot be tempered. This distributed arrangement of the copies enables a validation process that includes solving a computationally difficult problem that is also easy to verify and is sometimes called a "proof-of-work."

The output generated by the blockchain server 114 or connected devices such as the processing device 704 allows creating a set of copies of the data contained in the form of computer executable and blockchain executable files that are retained in the form of blocks over the blockchain which are accessible through a plurality of access points as discussed above. No single entity has dominion over the data stored in the blockchain server including the blockchain executable files processed by the blockchain device 702. It is a single recorded instance of the transaction distributed across parties with varying permission levels. If a disaster strikes one node or connection, it does not change or lose the record, as it still remains in its single, unaltered state across remaining nodes, thereby proving enhanced scalability and protection to the data distributed and used across the network among the wide base of users without any sort of interruption.

The ecosystem 100, 200 herein provides an arrangement of a dual-server system that includes the blockchain server 114 and the secured cloud server 116. The blockchain server 114 is configured to perform entire data management tasks such as data storage, data access, data collection and aggregation, and data retrieval. The blockchain server 114 also allows management of entire blockchain capabilities and integration of the blockchain devices 304 with the blockchain database 118. The blockchain server 114 is not directly accessible to the users or the devices 104, 110. Instead, the secured cloud server 116 is connected to the blockchain server 114 for providing a second a layer of security to information stored therein. The secured cloud server 116 allows the users to access one or more of the computer-executable files through a secured access from a remote location without being able to create a local copy of the one or more of the computer-executable files that are stored within the blockchain server 114 or blockchain database 118 operated through the blockchain server 114.

In an example, the embodiments herein can provide a computer program product configured to include a pre-configured set of instructions, which when performed, can result in actions as stated in conjunction with various figures herein. In an example, the pre-configured set of instructions can be stored on a tangible non-transitory computer readable medium. In an example, the tangible non-transitory computer readable medium can be configured to include the set of instructions, which when performed by a device, can cause the device to perform acts similar to the ones described here.

Embodiments herein may also include tangible and/or non-transitory computer-readable storage media for carrying or having computer-executable instructions or data structures stored thereon. Such non-transitory computer readable storage media can be any available media that can be accessed by a general purpose or special purpose computer, including the functional design of any special purpose processor as discussed above. By way of example, and not limitation, such non-transitory computer-readable media can include RAM, ROM, EEPROM, CD-ROM or other optical disk storage, magnetic disk storage or other magnetic storage devices, or any other medium which can be used to carry or store desired program code means in the form of computer-executable instructions, data structures, or processor chip design. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a special purpose computer or special purpose processing device to perform a certain function or group of functions. Computer-executable instructions also include program modules that are executed by computers in stand-alone or network environments. Generally, program modules include routines, programs, components, data structures, objects, and the functions inherent in the design of special-purpose processors, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

The techniques provided by the embodiments herein may be implemented on an integrated circuit chip (not shown). The chip design is created in a graphical computer programming language, and stored in a computer storage medium (such as a disk, tape, physical hard drive, or virtual hard drive such as in a storage access network. If the designer does not fabricate chips or the photolithographic masks used to fabricate chips, the designer transmits the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The embodiments herein can include both hardware and software elements. The embodiments that are implemented in software include but are not limited to, firmware, resident software, microcode, etc.

Furthermore, the embodiments herein can take the form of a computer program product accessible from a computer-usable or computer-readable medium providing program code for use by or in connection with a computer or any instruction execution system. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

A representative hardware environment for practicing the embodiments herein is depicted in FIG. 11, with reference to FIGS. 1 through 10. This schematic drawing illustrates a hardware configuration of an information handling/computer system 1100 in accordance with the embodiments herein. The system 1100 comprises at least one processor or central processing unit (CPU) 10. The CPUs 10 are interconnected via system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system 1100 can read the inventive instructions on the program storage devices and follow these instructions to execute the methodology of the embodiments herein. The system 1100 further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network, and a display adapter 21 connects the bus 12 to a display device 23 which may be embodied as an output device such as a monitor, printer, or transmitter, for example. Further, a transceiver 26, a signal comparator 27, and a signal converter 28 may be connected with the bus 12 for processing, transmission, receipt, comparison, and conversion of electric or electronic signals.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A computer-controlled diagnostic network system for facilitating integrated remote-based diagnostics, the system comprising:

a plurality of diagnostic devices located at different locations in a distributed secured network and associated with respective diagnostic centers, wherein a first diagnostic device of the plurality of diagnostic devices generates at least one computer-executable file comprising first diagnostic data in a first format, a second diagnostic device of the plurality of diagnostic devices generates at least one computer-executable file comprising second diagnostic data in a second format different from the first format;

a data standardization processor executing computer-executable digital instructions for standardizing the first diagnostic data and the second diagnostic data in accordance with a predefined format including an HL7 standard for processing;

an artificial intelligence (AI) module integrated into the system for performing a workflow task including one or more of an automated review, annotation, labeling, and a commenting on standardized first diagnostic data and the second diagnostic data, wherein the AI module comprises:

an interface layer that receives inputs from the diagnostic devices that serve as initial inputs to the AI module and analyzes the initial inputs to examine whether enough details are available to proceed, an AI application processing layer that collects the initial inputs and related information from internal databases including a blockchain database and external Internet sources and process the initial inputs using computational intelligent tools to make automated analysis and judgments for automated reading of the diagnostic data, and machine learning code that trains the AI module to continuously improve performance in outcomes based on feedback received from the diagnostic devices, wherein the AI module is configured to classify the first diagnostic data in the first format and the second diagnostic data in the second format based on predefined criteria and generate diagnostic reports based on annotations and labels, and wherein the classification of the first diagnostic data in the first format and the second diagnostic data in the second format develops a structured taxonomy and definition for evolving the AI module; and a computer-controlled central blockchain server comprising:

a plurality of distributed blockchain-configured access points providing a virtual storage through a plurality of distributed network nodes, wherein each node maintains a copy of a blockchain configured to get downloaded automatically upon joining the network;

a blockchain database communicatively coupled to the computer-controlled central blockchain server and located at a location remote from locations of the plurality of diagnostic devices, wherein the blockchain database stores at least one unique hash and at least one timestamp of the at least one unique hash; and a processing circuit coupled to a memory circuit storing computer-executable rules and integrated circuits executing the computer-executable rules for verification of diagnostic data and workflow tasks, wherein the computer-controlled central blockchain server stores and processes details obtained from the diagnostic devices and the structured taxonomy and definition for evolving the AI module and the structured taxonomy and definition is used to serve as an input to the AI module next time for improving outcomes of the workflow task; and a secured cloud server communicatively coupled to the blockchain server that allows access to one or more of the computer-executable files through a secured access from a remote location without enabling creation of a local copy of the one or more computer-executable files, wherein the data standardization processor, the AI module, the computer-controlled central blockchain server, and the secured cloud server function together as a distributed technological system that improves computer functionality by enabling integration of heterogeneous diagnostic data from distributed sources, providing automated analysis through machine learning, ensuring data security through blockchain verification, and enabling secure remote access to diagnostic files.

2. The system of claim 1, wherein the AI module comprises:

an interface layer to receive inputs form a computing system that serves as an initial input to the AI module; and an AI application processing layer to collect the initial input and related information from the computer-controlled central blockchain server and external sources, and process the initial input, make automated analysis and judgment for automated reading of the first and second diagnostic data extracted from the first and second diagnostic devices using a plurality of computational intelligent tools.

3. The system of claim 1, wherein the AI module comprises a search engine that runs intelligent information searching and mining tools for complicated phrases or sentences to search for related information to improve performance through training.

4. The system of claim 3, wherein the AI module comprises machine learning components that train the AI module to continuously improve performance in outcomes based on the structured taxonomy and definition and the first and second diagnostic data received from the first and second diagnostic devices.

5. The system of claim 1, comprising a data standardizing device to perform computer-executable digital instructions for standardizing digitally stored diagnostic data retrieved from the plurality of diagnostic devices in accordance with a predefined format, wherein the digitally stored diagnostic data before standardizing and supplying to the AI module resides in a plurality of formats within the plurality of diagnostic devices.

6. The system of claim 1, wherein the distributed secured network comprises a blockchain configured diagnostic network.

7. The system of claim 1, comprising a blockchain database communicatively coupled to the computer-controlled central blockchain server and located at a location remote from locations of the plurality of diagnostic devices and the plurality of diagnostician devices.

8. The system of claim 1, comprising a private data store communicatively connected with the computer-controlled central blockchain server allowing a federated blockchain through a plurality of private access points that provides a virtual storage to facilitate interaction with the plurality of diagnostic devices maintaining a secured access of each computer executable file privately with only permissioned access and accessible from distributed locations no matter where the first and second diagnostic data originated from or is stored.

9. The system of claim 1, wherein the plurality of diagnostic devices comprises:

the first diagnostic device located at a first location;

the second diagnostic device located at a second location; and a third diagnostic device located at a third location, wherein the central blockchain server is located at a fourth location and communicatively connected with the first diagnostic device, the second diagnostic device, and the third diagnostic device, wherein the AI module is located at the fifth location and communicatively connected with the central blockchain server, the first diagnostic device, the second diagnostic device, and the third diagnostic device, and wherein the first diagnostic device, the second diagnostic device, the third diagnostic device, the central blockchain server, and the AI module are configured as a marketplace network, wherein the marketplace networked is configured within the blockchain secured network and including a marketplace component for facilitating interactions, purchases, and delivering of the first and second diagnostic data analyzed and reported for meaningful interpretations in the form of a diagnostic report.

10. The system of claim 1, comprising a workflow system for performing a set of special-purpose computer-executable operations for allocating tasks among a plurality of diagnosticians connected through the diagnostic network, wherein the workflow system generates a computer-executable workflow file indicating one or more tasks allocated to the diagnosticians and automated access rights based on credentialing of digital profiles of the diagnosticians after these files are verified, analyzed, and annotated by the AI module for one or more of:

generating human feedback to serve to the AI module to improve performance of the AI module; and verifying an outcome generated by the AI module for verification and correctness in one or more cases.

11. The system of claim 10, wherein the set of special-purpose computer-executable operations within the distributed secured network comprises:

creating the tasks as entries digitally;

defining a set of routing rules for the plurality of diagnosticians associated with the plurality of diagnostician devices that trigger or accept to execute a task;

retrieving the tasks for allocation to the plurality of diagnosticians from the workflow system; and presenting digitally one or more of the tasks to the plurality of diagnosticians based on their credentials and their preferences indicative through their digital profiles.

12. A computer-controlled diagnostic network system for facilitating integrated remote-based diagnostics, the system comprising:

a plurality of diagnostic devices located at different locations in a distributed secured network and associated with respective diagnostic centers, wherein each diagnostic device generates at least one computer-executable file comprising digitally stored diagnostic data in a specific format;

a data standardization processor executing computer-executable digital instructions for standardizing the diagnostic data in accordance with a predefined format including an HL7 standard for processing;

a plurality of diagnostician devices associated with diagnosticians located at various locations in the distributed secured network and remotely located from the diagnostic devices, wherein each diagnostician device reads the diagnostic data digitally stored in the at least one computer-executable file from a respective diagnostic device;

a computer-controlled central blockchain server comprising:

a plurality of distributed blockchain-configured access points providing a virtual storage through a plurality of distributed network nodes configured as a peer-to-peer network where each node is an administrator of the blockchain, a blockchain database communicatively coupled to the computer-controlled central blockchain server and located at a location remote from locations of the plurality of diagnostic devices and diagnostician devices, wherein the blockchain database contains smart contracts that execute when specified conditions are met, and a processing circuit coupled to a memory circuit and integrated circuits executing a set of computer-executable rules for verification of diagnostic data and workflow tasks, wherein the computer-controlled central blockchain server stores and processes details obtained from the diagnostic devices and the diagnostician devices;

an artificial intelligence (AI) module integrated into the system for performing automated analysis of the standardized diagnostic data, wherein the AI module comprises:

an interface layer that receives inputs from the diagnostic devices that serve as initial inputs to the AI module and requests user feedback to proceed on further analysis, an AI application processing layer that collects the initial inputs and related information from external sources and process the initial inputs using computational intelligent tools to make automated analysis and judgments for automated reading of the diagnostic data, the AI application processing layer collecting related information from the blockchain database to process the initial inputs and make automated judgment, and machine learning code that trains the AI module to continuously improve performance in outcomes based on feedback received from the diagnostic devices, wherein the AI module is configured to classify the diagnostic data based on predefined criteria and generate diagnostic reports based on annotations and labels, wherein the classification of the diagnostic data develops a structured taxonomy and definition for evolving the AI module;

a workflow system including a task segmentation engine creating workflow steps for tasks and a task scheduling engine allocating the tasks to diagnosticians, a workflow system performing a set of special-purpose computer-executable operations for allocating tasks among the diagnosticians connected through the diagnostic network, wherein the workflow system generates a computer-executable workflow file indicating one or more tasks allocated to the diagnosticians and automated access rights based on credentialing of digital profiles of the diagnosticians and dynamically updates in the computer-executable workflow file when the diagnosticians accepts the allocation of the tasks; and a secured cloud server communicatively coupled to the blockchain server that allows access to one or more of the computer-executable files through a secured access from a remote location without enabling creation of a local copy of the one or more computer-executable files, wherein the data standardization processor, the AI module with its interface layer, application processing layer, and machine learning code, the computer-controlled central blockchain server with its distributed access points, blockchain database, processing circuit and memory circuit, the workflow system, and the secured cloud server function as an integrated technological solution that provides specific improvements to computer functionality in diagnostic data processing, including standardization of heterogeneous data formats, evolution of AI capabilities through machine learning, secure distributed storage through blockchain technology, and secure remote access without local copying.

13. The system of claim 12, comprising a private data store communicatively connected with the computer-controlled central blockchain server allowing a federated blockchain that provides a virtual storage to facilitate interaction, information exchange, reviewing, and presentation of only limited executed files or portions thereof as determined based on the computer-executable workflow file allowing the automated access rights based on credentialing of the digital profiles.

14. The system of claim 12, comprising a data standardizing device to perform computer-executable digital instructions for standardizing digitally stored diagnostic data retrieved from the plurality of diagnostic devices in accordance with a predefined format, wherein the digitally stored diagnostic data before standardizing resides in a plurality of formats within the plurality of diagnostic devices.

15. The system of claim 12, comprising a blockchain database communicatively coupled to the computer-controlled central blockchain server and located at a location remote from locations of the plurality of diagnostic devices and the plurality of diagnostician devices.

16. The system of claim 12, wherein the set of special-purpose computer-executable operations within the distributed secured network comprises:

creating the tasks as entries digitally;

defining a set of routing rules for the plurality of diagnosticians associated with the plurality of diagnostician devices that trigger or accept to execute a task;

retrieving the tasks for allocation to the plurality of diagnosticians from the workflow system; and presenting digitally one or more of the tasks to the plurality of diagnosticians based on their credentials and their preferences indicative through their digital profiles.

17. The system of claim 16, wherein the workflow system comprises a task segmentation engine to create the one or more work flow steps for the tasks defining the set of routing rules for the one or more diagnostician devices that trigger or accept to execute the task digitally.

18. The system of claim 17, wherein the workflow system comprises a task scheduling engine to allocate and present the one or more tasks to the one or more diagnostician devices based on their credentials and their preferences indicative through their digital profiles.

19. The system of claim 12, wherein the distributed secured network comprises a blockchain configured diagnostic network.

20. The system of claim 12, comprising a credentialing system to compute credentialing of the digital profiles associated with the diagnostician devices such that the automated access rights are granted based on credentialing of the digital profiles.

* * * * *